United States Patent [19]
Mountz et al.

[11] Patent Number: 5,981,829
[45] Date of Patent: Nov. 9, 1999

[54] ΔNUR77 TRANSGENIC MOUSE

[75] Inventors: John D. Mountz; Tong Zhou, both of Birmingham; Jianhua Cheng, Alabaster, all of Ala.

[73] Assignee: UAB Research Foundation, Birmingham, Ala.

[21] Appl. No.: 08/852,173

[22] Filed: May 6, 1997

Related U.S. Application Data

[60] Provisional application No. 60/016,914, May 8, 1996, abandoned.

[51] Int. Cl.$^6$ .............................. C12N 5/00; C12N 15/00; C12N 15/09; C12N 15/63
[52] U.S. Cl. ................................ 800/18; 800/11; 800/21; 800/22; 800/25; 800/3; 435/455; 536/23.1
[58] Field of Search .................................. 800/2, 18, 11, 800/21, 22, 25, 3; 536/23.1; 435/455

[56] References Cited

PUBLICATIONS

Augee et al. Platypus and Echidnas. The Royal Zoological Society of New South Wales, New South Wales, 1992.
Zhou et al. J. Experimental Medicine, Apr. 1, vol. 183, 1879–92, 1996.
Calnan et al. Immunity, Sep, vol. 3, 273–82, 1995.
Rothe et al. International Immunol., vol. 5, 11–17, 1993.
Kisielow et al. Nature, vol. 333, 742–745, 1988.
Mountz et al. J. Experimental Medicine, vol. 172, 1805–17, 1990.

*Primary Examiner*—Deborah Crouch
*Assistant Examiner*—Jill D. Martin
*Attorney, Agent, or Firm*—Benjamin Aaron Adler

[57] ABSTRACT

The present invention provides a transgenic mouse containing a transgene, said transgene comprising a truncated Nur77 (ΔNur77) gene. Also provided is a double transgenic mouse, wherein said double transgenic mouse comprises the ΔNur77 transgenic mouse backcrossed with the $D^b$/HY T cell receptor transgenic mouse.

12 Claims, 15 Drawing Sheets

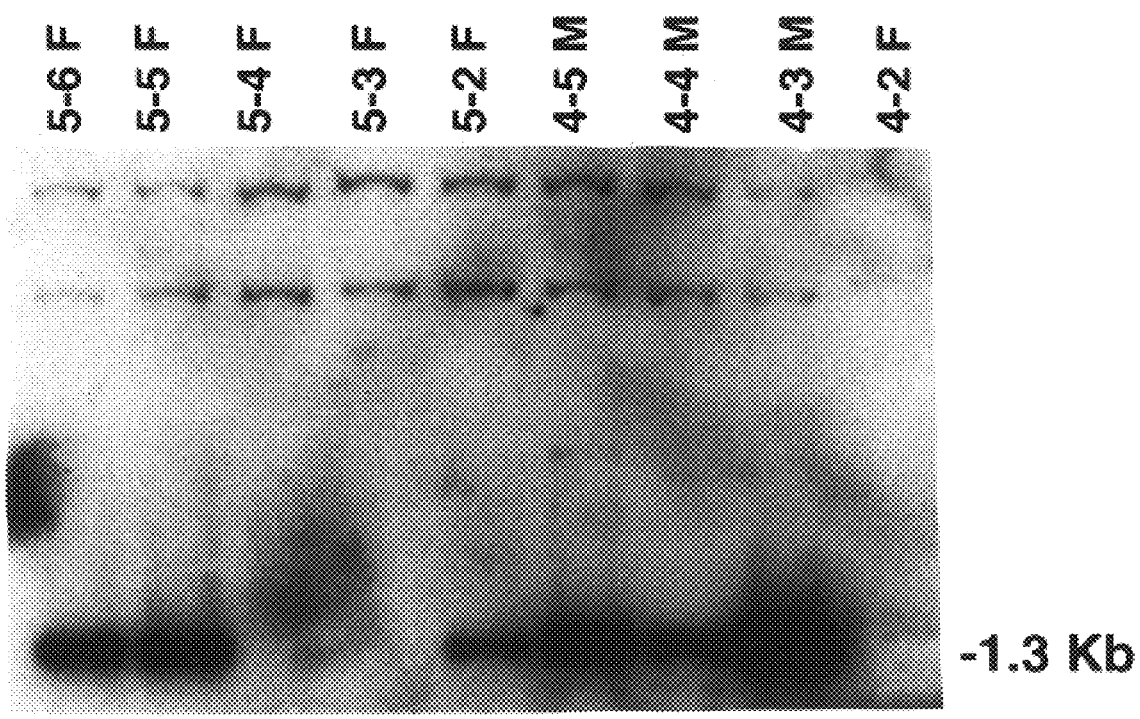
FIG. 1-A

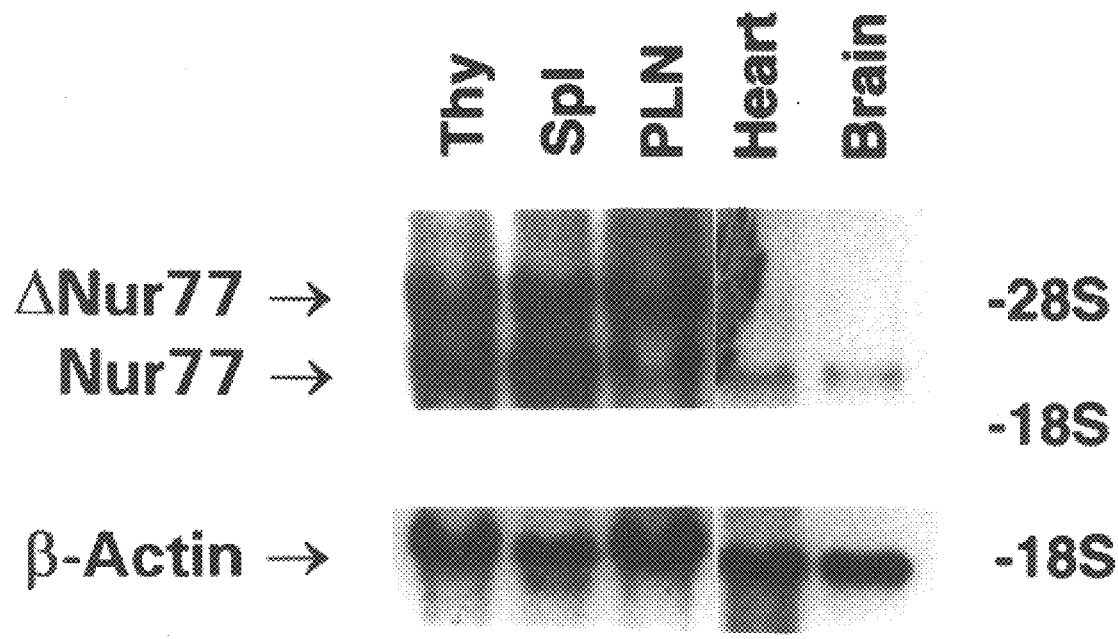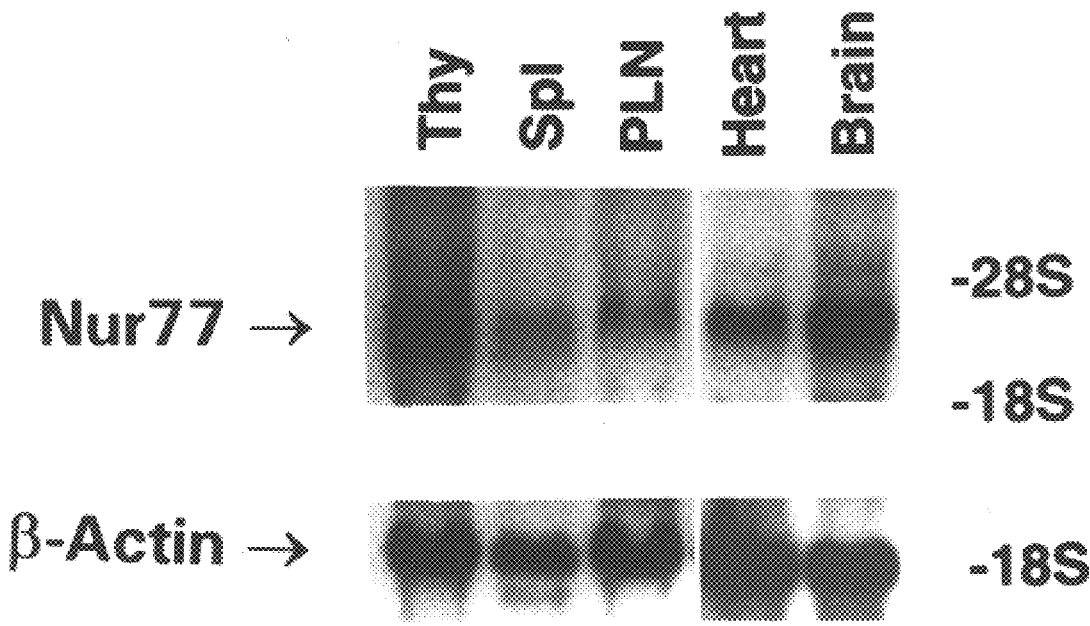
FIG. 1-B

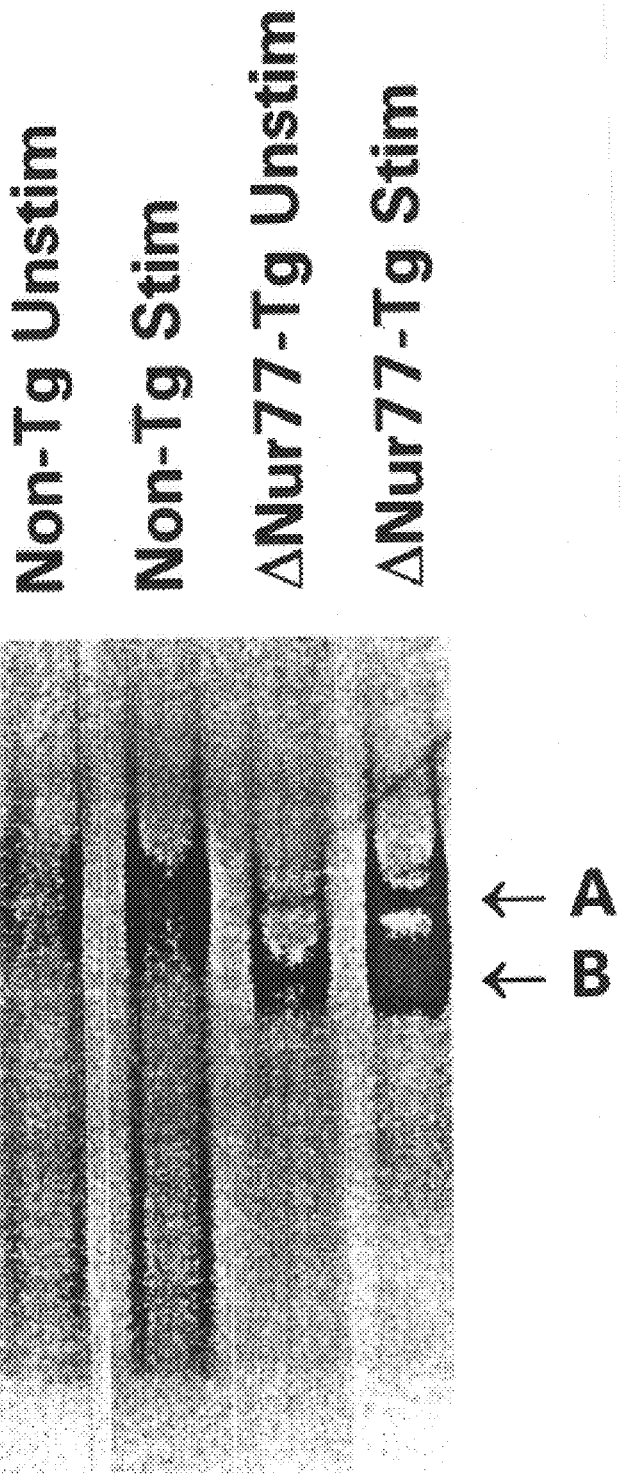
FIG. 1-C

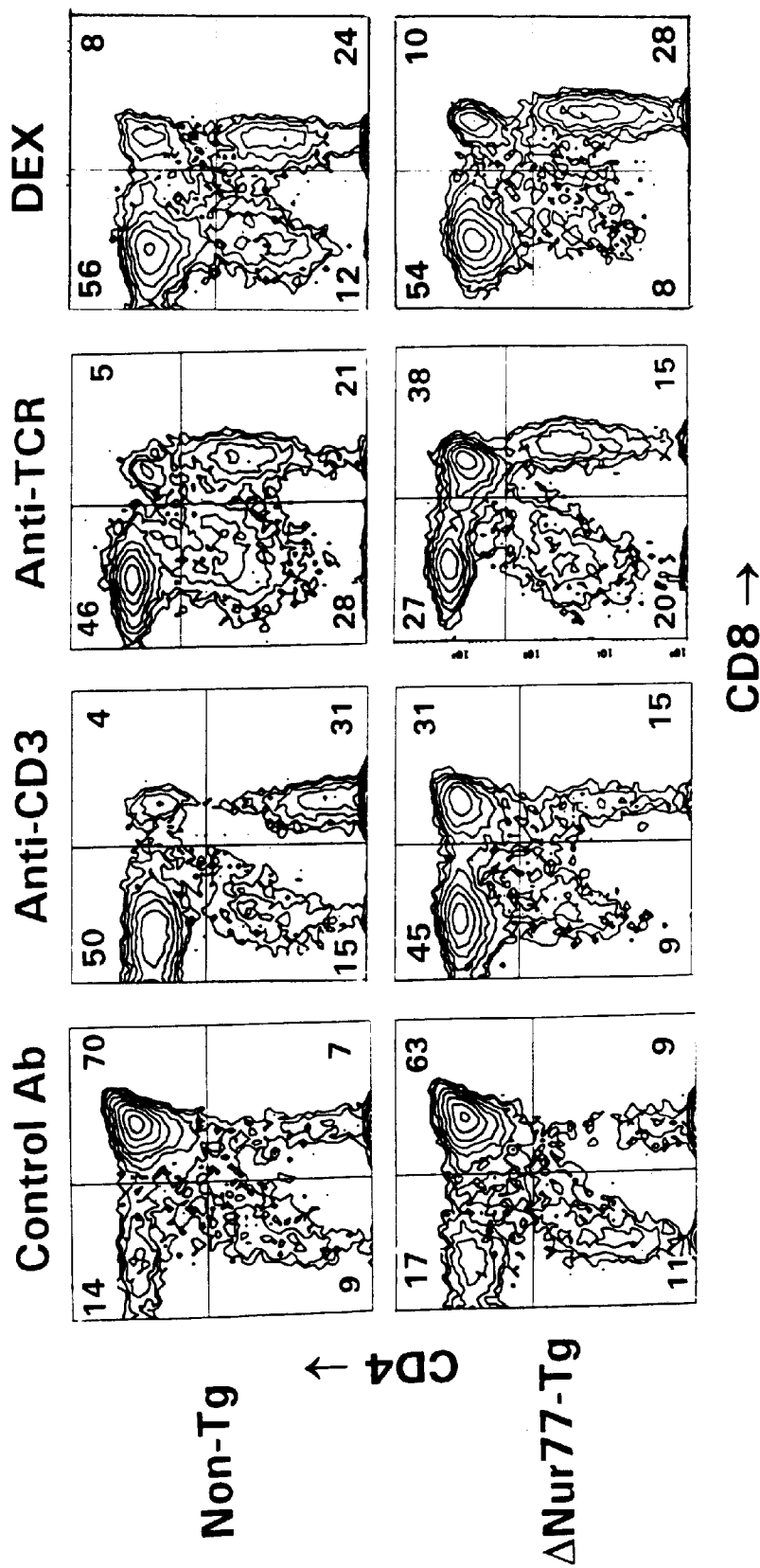
FIG. 2-A

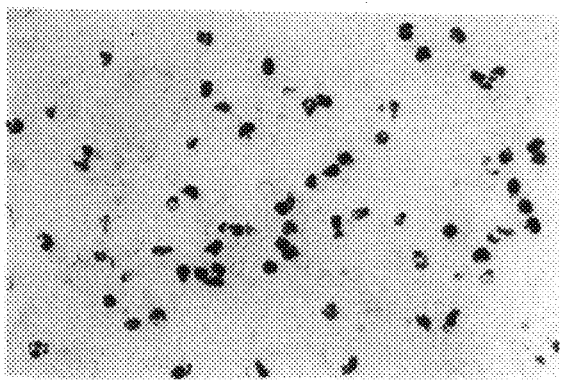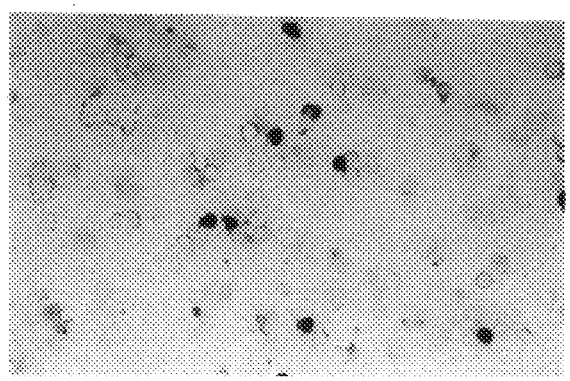
FIG. 2-B

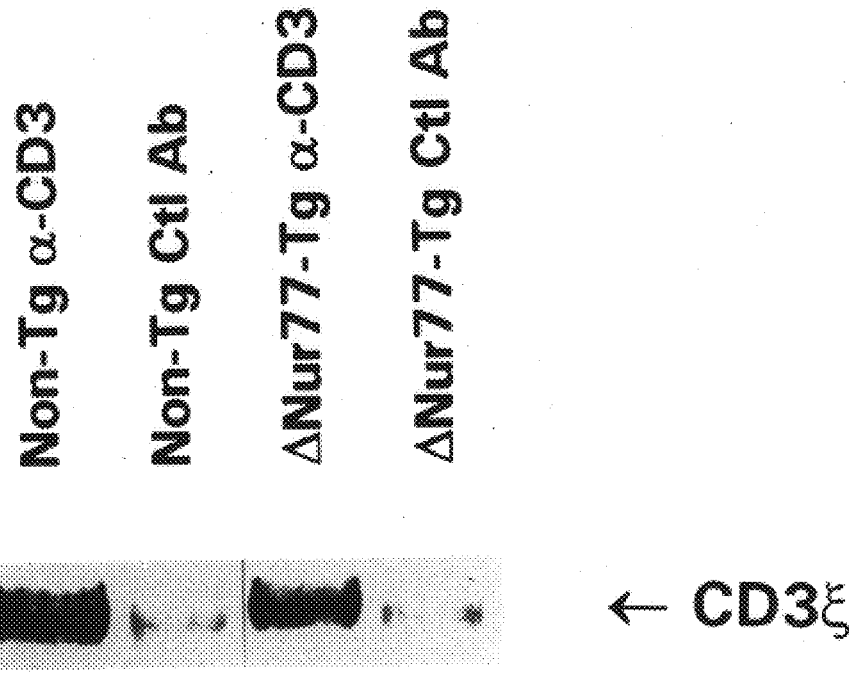
FIG. 2-C

- ○ - $D^b$/HY-Tg Male
- ● - ΔNurr77- $D^b$/HY Male
- □ - $D^b$/HY-Tg Female
- ■ - ΔNurr77- $D^b$/HY Female

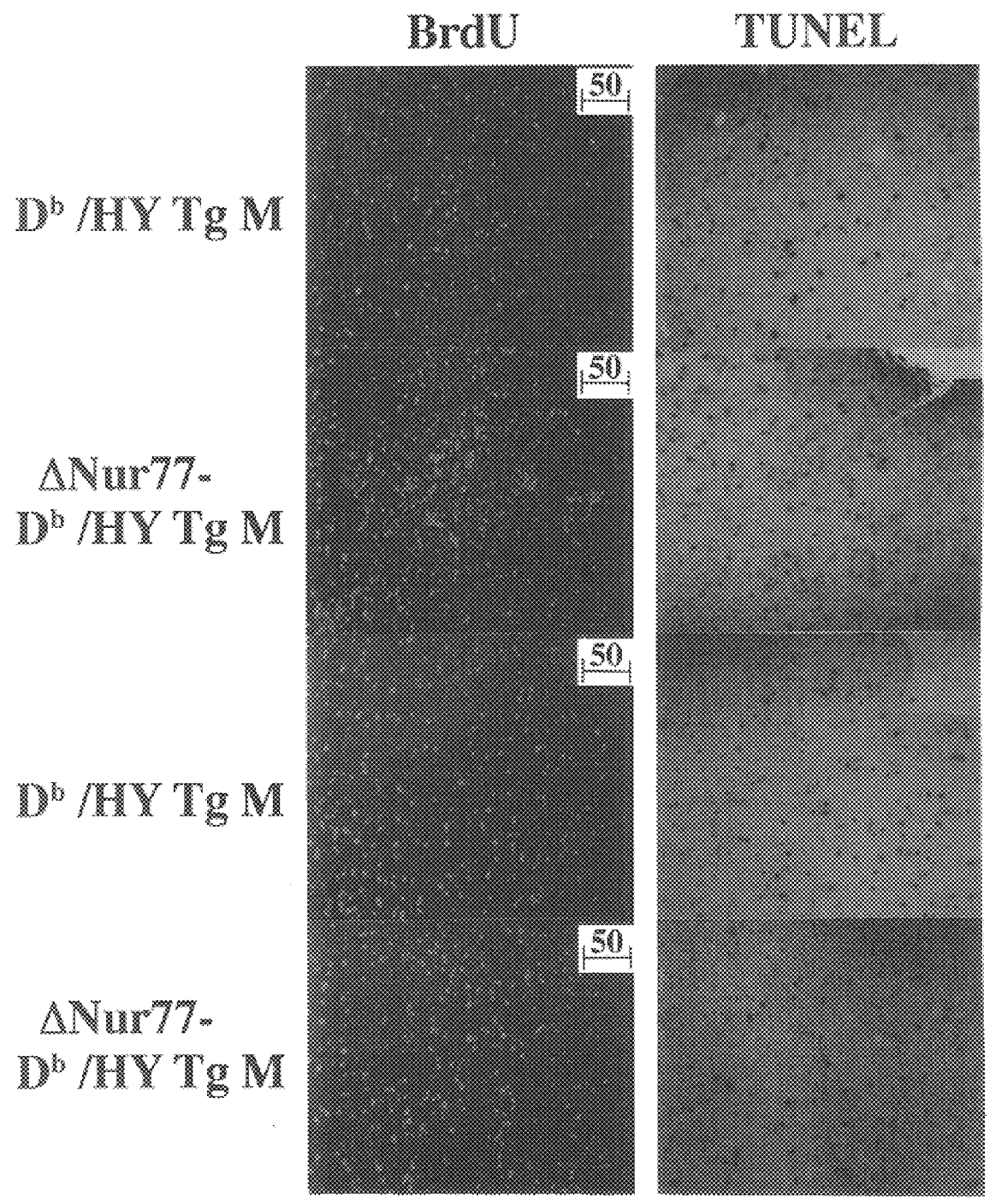
FIG. 8-A

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 20 basepairs
       (B) TYPE: nucleic acid
       (C) STRANDEDNESS: single-stranded
       (D) TOPOLOGY: linear (ii) MOLECULE TYPE:
       (A) DESCRIPTION: other nucleic acid (iii) HYPOTHETICAL: no (iv) ANTI-SENSE: no (xi) SEQUENCE DESCRIPTION:SEQ ID NO: 1:

CCACCATGCC AGCAGCTTTC                                           20

(2) INFORMATION FOR SEQ ID NO:2:

(i) SEQUENCE CHARACTERISTICS:
       (A) LENGTH: 20 basepairs
       (B) TYPE: nucleic acid
       (C) STRANDEDNESS: single-stranded
       (D) TOPOLOGY: linear (ii) MOLECULE TYPE:
       (A) DESCRIPTION: other nucleic acid (iii) HYPOTHETICAL: no (iv) ANTI-SENSE: no (xi) SEQUENCE DESCRIPTION:SEQ ID NO: 2:

GGATCCGTGG GCTATAGGCT                                           20

(2) INFORMATION FOR SEQ ID NO:3:

(i) SEQUENCE CHARACTERISTICS:
       (A) LENGTH: 27 basepairs
       (B) TYPE: nucleic acid
       (C) STRANDEDNESS: single-stranded
       (D) TOPOLOGY: linear (ii) MOLECULE TYPE:
       (A) DESCRIPTION: other nucleic acid (iii) HYPOTHETICAL: no (iv) ANTI-SENSE: no (xi) SEQUENCE DESCRIPTION:SEQ ID NO: 3:

GGAGTTTTAA AAGGTCATGC TCAATTT                                   27

(2) INFORMATION FOR SEQ ID NO:4:

(i) SEQUENCE CHARACTERISTICS:
       (A) LENGTH: 27 basepairs
       (B) TYPE: nucleic acid
       (C) STRANDEDNESS: single-stranded
       (D) TOPOLOGY: linear (ii) MOLECULE TYPE:
       (A) DESCRIPTION: other nucleic acid (iii) HYPOTHETICAL: no

```
       (iv) ANTI-SENSE:  yes (xi) SEQUENCE DESCRIPTION:SEQ ID NO:   4:

GGAAATTGAG CATGACCTTT TAAAACT                                        27
```

ΔNUR77 TRANSGENIC MOUSE

CROSS-REFERENCED TO RELATED APPLICATION

This application claims to benefit of priority of provisional application Ser. No. 60/016,914 filed on May 8, 1996, now abandoned.

FEDERAL FUNDING LEGEND

This invention was created in part with funds from the federal government under grants from the National Institutes of Health (grants AR20614, A123694, AR03555, and A130744). Consequently, the federal government has certain rights in this invention.

BACKGROUND OF THE INVENTION

1. Field of the Invention

The present invention relates generally to the fields of molecular immunology and genetics. More specifically, the present invention relates to a novel ΔNur77 trangenic mouse.

2. Description of the Related Art

Clonal deletion and clonal anergy are the primary mechanisms for induction of self-tolerance in T cells (1). During thymic maturation, thymocytes bearing self-reactive T cell receptors (TCR) undergo clonal deletion and are eliminated by programmed cell death or apoptosis (2, 3). Thymocytes with intermediate to high density levels of expression of the TCR undergo negative selection at the $CD4^+CD8^+$ (double positive) stage of thymocyte development (4–8). Downmodulation of the TCR, CD4 and/or CD8 molecules on the surface of T cells has been proposed as a mechanism for escape from negative selection (8–12). Thus, the TCR generates signals that are capable of mediating negative selection of thymocytes by clonal deletion. However, the signaling mechanisms required for negative selection of thymocytes remain unknown.

Several molecules and pathways known to be of importance in apoptosis have been described in the thymus, however, their contribution to clonal deletion and tolerance induction remains controversial (1). Although knockout of p53 leads to decreased sensitivity of murine thymocytes to radiation-induced apoptosis, negative selection remains intact (13–15). Fas is a cell surface receptor that mediates apoptosis by interaction with a specific ligand and is expressed on most murine thymocytes (16–19). Although mutant Fas antigen and Fas ligand cause autoimmune disease in lpr/lpr and gld/gld mice, respectively (18–20), no major negative selection defects have been found in lpr/lpr mice (21–25). Therefore, it is unlikely that Fas antigen is directly involved in negative selection in the thymus.

Bcl-2 prevents thymocyte apoptosis that is induced by radiation, steroids, and other chemicals (26–28). Expression of bcl-2 has been reported to be decreased in $CD4^+8^+$ thymocytes, but not in mature thymocytes, and has been proposed to play a role in inhibition of negative selection in the thymus (29). However, bc/-2 knockout mice do not exhibit excessive clonal deletion in the thymus (30) and, conversely, bcl-2 transgenic mice do not exhibit a major defect in negative selection or T cell tolerance (28, 31–33). Double transgenic bcl-2+$D^b$/HY TCR mice show that constitutive expression of bcl-2 increases the survival of thymocytes in the absence of positive selection (34–36). The bcl-2 transgene also reduces the efficiency of negative selection, but the mature peripheral T cells which appear in increased numbers were not autoreactive. Thus, although bcl-2 can play a role in both positive and negative selection, tolerance is maintained by a mechanism that can bypass bcl-2.

NGFI-B/Nur77 is a growth factor-inducible member of the steroid/thyroid hormone receptor superfamily originally identified in nerve growth factor (NGF)-treated P12 pheochromocytoma cells (37) and in serum-stimulated fibroblasts (38). NGFI-B/Nur77 is transcriptionally regulated as an immediate-early gene and is rapidly activated by phosphorylation after stimulation with serum or nerve growth factor (39, 40). NGFI-B/Nur77 has a centrally located, highly conserved DNA binding domain containing two zinc-fingers and a transcriptional trans-activating domain (41–47). NGFI-B/Nur77 gene is expressed in thymic medulla and is rapidly upregulated in T cell hybridomas and thymocytes after treatment with anti-CD3 or anti-TCR and this expression has been correlated with induction of apoptosis (48, 49). Blocking of nerve growth factor I-B with either a dominant negative truncated (48) or antisense (49) NGFI-B/Nur77 gene prevented TCR/CD3 signaling-mediated apoptosis in T cell hybridomas.

There are at least two gene families with an identical nerve growth factor I-B response element (NBRE) AAAG-GTCA (50). The first member of this family, referred to as Nur77 (mouse), nerve growth factor I-B (rat), and NAK-1 (human) peaks 1 hour after stimulation of the PEER T cell line. The second member, referred to as Nurr1 (mouse), RNR-1 (rat), and transcriptionally inducible nuclear receptor (human) peaks 24 hours after stimulation and correlates with apoptosis. Although Nur77 has been shown to be important in T cell signaling and apoptosis (48, 49), other signaling proteins can also contribute to T cell maturation and apoptosis. This was recently demonstrated in a Nur77 mutant mouse, in which T cells did not exhibit defective apoptosis after anti-CD3 crosslinking and exhibit normal T cell development and apoptosis in $D^b$/HY TCR transgenic mice (51).

The prior art is deficient in the lack of a ΔNur77 trangenic mouse. The present invention fulfills this longstanding need and desire in the art.

SUMMARY OF THE INVENTION

The present invention utilizes a truncated Nur77 transgene capable of expressing high levels of a non-functional DNA binding protein to block the nerve growth factor I-B response element (NBRE) in T cells. The present invention indicates that the truncated form of ΔNur77 gene binds to the NBRE and inhibits TCR/CD3 signaling-mediated apoptosis and also interferes with selection and clonal deletion in the thymus of ΔNur77-$D^b$/HY TCR double transgenic mice. The Nur77/Nurr1 family of DNA binding proteins has been reported to be required for the signal transduction of CD3/TCR-mediated apoptosis in T cell hybridomas. To illustrate the role of this family of DNA binding proteins in thymic clonal deletion, transgenic mice bearing a dominant negative mutation were produced. The transgene consisted of a truncated Nur77 (ΔNur77) gene encoding the DNA binding domain of Nur77 ligated to a TCRβ enhancer resulting in early expression in thymocytes. Apoptosis of $CD4^+CD8^+0$ thymocytes mediated by CD3/TCR signalling was greatly inhibited in the ΔNur77-Tg mice, compared to non-transgenic littermates, after treatment with anti-CD3 or anti-TCR antibody in vivo and in vitro. Clonal deletion of self-reactive T cells was investigated in ΔNur77-$D^b$/HY TCRαβ double transgenic mice. There was a 5-fold increase in the total number of thymocytes expressing self-reactive $D^b$/HY TCRαβ in the ΔNur77-TCRαβ double transgenic male mice. Deficient clonal deletion of self-reactive thymocytes was demonstrated by a 10-fold increase in the $CD4^+CD8^+$ thymocytes that expressed transgenic TCRαβ. There was an 8-fold increase in $CD8^+$, $D^b$/HY TCRαβ T cells in the lymph nodes of ΔNur77-$D^b$/HY TCRαβ double transgenic male mice compared to $D^b$/HY TCRαβ transgenic male mice. In spite of defective clonal deletion, the T cells expressing the transgenic TCR were functionally anergic. In vivo analysis revealed increased activation and apoptosis of T cells associated with increased expression of Fas and Fas ligand in LN of ΔNur77-$D^b$/HY TCRαβ double transgenic male mice. These results indicate that inhibition of Nur77/Nurr1 DNA binding in T cells leads to inefficient thymic clonal deletion, but T cell tolerance is maintained by Fas dependent clonal deletion in LN and spleen.

In one embodiment of the present invention, there is provided a transgenic animal containing a transgene, said transgene comprising a truncated Nur77 (ΔNur77) gene.

In another embodiment of the present invention, there is provided a double transgenic mouse, wherein said double transgenic mouse comprises the ΔNur77 transgenic mouse backcrossed with the $D^b$/HY T cell receptor transgenic mouse.

In yet another embodiment of the present invention, there is provided an in vivo model for analysis of autoreactive T cells undergoing tolerance though the Fas/Fas ligand apoptosis system, wherein the model is used to screen for compounds that either up or downmodulates the Fas/Fas ligand apoptosis system.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1A–C shows the characterization of ΔNur77-Tg mice. FIG. 1A shows the detection of the transgene by Southern blot analysis. Southern blot analysis of tail DNA carried out after digestion with BamH1 revealed six lines of ΔNur77 transgenic mice. BamHI digestion liberated a 1.3 kb cDNA corresponding to the Nur77 DNA binding domain and also higher molecular weight endogenous genomic Nur77 DNA fragments at approximately 8 and 6 kb. Different lines of transgenic founder mice are designated according to sex (M=male, F=female) as 4-3M, 4-4M, 4-5 M, 5-2 F, 5-5 F, and 5-6 F. Experiments were carried with the line drive from 4-4 M. FIG. 1B shows the expression of the truncated ΔNur77 RNA transcript in ΔNur77 transgenic mice. RNA was prepared from thymus (Thy), spleen (Spl), peripheral lymph node (PLN), heart, and brain of ΔNur77 transgenic mouse (line 4-4 M) or non-transgenic control mice. Non-transgenic control mice expressed a full-length Nur77 transcript with MW of approximate 3.7 kb in the lymphoid organs as well as non-lymphoid organs. ΔNur77 transgenic mice expressed the 3.7 kb endogenous Nur77 transcript as well as an approximately 5.5 kb ΔNur77 transcript in tissue containing T cells. For RNA loading controls, blots were stripped and subsequently reprobed with the gene corresponding to β-actin. FIG. 1C shows the gel-shift assay of Nur77 protein. The NBRE was end-labeled and incubated with the nuclear extract derived from unstimulated and stimulated thymocytes of non-Tg or ΔNur77 transgenic mice. Non-transgenic and ΔNur77 transgenic mice exhibited an identical-size higher gel shift band indicated by A. ΔNur77 transgenic mice also exhibited a unique lower gel shift band indicated by B.

FIG. 2A shows a flow cytometric analysis of thymocyte subpopulation. Thymocyte suspensions were labeled with anti-CD4 or anti-CD8 and analyzed by flow cytometry analysis. The percent of thymocytes in each of the CD4, CD8 subpopulations as defined by the cursors are shown on the graph. These data represent a typical flow cytometry analysis that was carried out using at least five different mice. FIG. 2B shows the terminal digoxigenin nucleotide end labeling staining of the thymocytes from anti-CD3 treated non-Tg and ΔNur77-Tg mouse. The thymocytes were prepared as above. $1\times10^5$ thymocytes were cytospun onto the slide and stained for apoptosis by the terminal digoxigenin nucleotide end labeling technique. FIG. 2C shows the tyrosine-phosphorylation of the CD3ζ chain after anti-CD3 crosslinking. Single cell suspensions of thymocytes were incubated with 10 µg/ml of either control antibody or anti-CD3 antibody for 5 minutes, followed by western blot analysis of CD3ζ using an anti-phosphotyrosine antibody.

FIG. 8A–B shows the increased activation and apoptosis of LN cells in $D^b$/HY TCR and ΔNur77-$D^b$/HY TCR Tg mice. FIG. 8A shows the immunohistochemical analysis for bromodeoxyuridine incorporation and apoptosis. Mice were injected with 1 mg bromodeoxyuridine every 6 hours for 24 hours. LN sections were analyzed for DNA incorporation of bromodeoxyuridine using the anti-bromodeoxyuridine antibody or for apoptosis using the Terminal digoxigenin nucleotide end labeling technique. The Figure is representative of at least 8 LN from 3 different mice. FIG. 8B shows the Fas expression and FasL activity. Single cell suspensions were prepared from LN of $D^b$/HY TCR transgenic male and ΔNur77-$D^b$/HY TCR double transgenic male mice. Cells were labeled with antibodies against anti-Fas, anti-CD8 and M33, followed by the analysis of 10,000 cells by flow cytometry. Cells were gated into M33$^+$CD8$^+$ and M33$^+$CD8$^-$ populations and Fas expression on each population is shown. These results are representative of three mice analyzed individually. Fas ligand activity by unstimulated LN cells was determined by the extent of lysis of $^{57}$Cr labeled Fas$^+$target cells using different effector/target ratios (E/T). Specificity for Fas/FasL interaction was determined by the inhibitory effect in the presence of a Fc-Fas fusion protein (FasFP). The percent of specific lysis is indicated as the mean±SEM for at least three individual mice analyzed in triplicate.

DETAILED DESCRIPTION OF THE INVENTION

Figure 3:
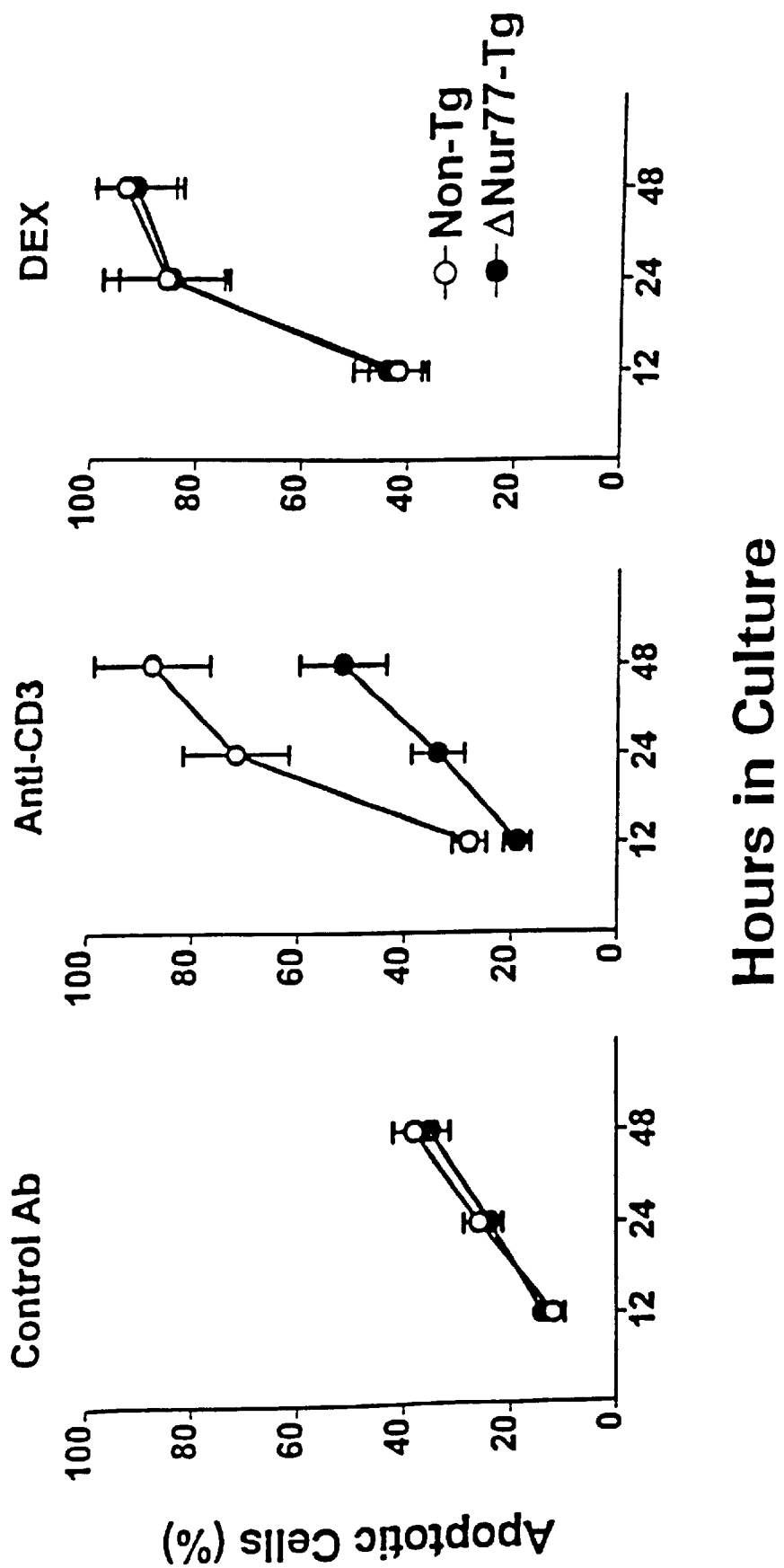
FIG. 3 shows the thymocyte apoptosis induced by anti-CD3 and dexamethasone in vitro. The thymocytes were prepared from non-Tg and ΔNur77-Tg mice. $2\times10^6$/ml thymocytes were cultured with plate bound anti-CD3 or control hamster IgG (10 µg/ml) or 10 µM dexamethasone for the indicated time. Apoptosis was determined by terminal digoxigenin nucleotide end labeling staining. Open and closed circles represents non-Tg and ΔNur77 Tg mice, respectively.

The following abbreviations may be used herein. Tg: transgenic; Tg71: TCR transgenic mice expressing the $D^b$/HY TCR; M33: $D^b$/HY TCR anticlonotypic Mab; BrdU: bromodeoxyuridine; TUNEL: Terminal digoxigenin nucleotide end labeling; NGFI-B: nerve growth factor I-B;

NBRE: NGFI-B response element; ΔNur77: Dominant negative mutation of Nur77; TINUR: transcriptionally inducible nuclear receptor.
Definitions As used herein, the term "clonal deletion" refers to deletion of autoreactive T cells in the thymus.

As used herein, the term "clonal anergy" refers to clones of T cells that are self-reactive but are not pathogenic or cause autoimmunity or disease.

As used herein, the term "self tolerance" refers to immune cells that acquire tolerance to self antigens.

As used herein, the term "negative selection" refers to deletion of self reactive T cells in the thymus.

The present invention is directed to a transgenic animal containing a transgene, said transgene comprising a truncated Nur77 (ΔNur77) gene. In one embodiment, the transgenic animal is a mouse. More specifically, in one embodiment, the transgenic animal contains a ΔNur77 gene which encodes a DNA binding domain of Nur77 ligated to a TCRβ enhancer with early expression in thymocytes. Generally, the ΔNur77 gene expresses a non-functional DNA binding protein, the protein being approximately a 5.5 kb ΔNur77 protein. The protein is expressed highly in the thymus, spleen, and lymph node but was not expressed in the heart or brain. Furthermore, the protein is capable of competitively inhibiting the binding of endogenous Nur77 protein to the nerve growth factor I-B response element (NBRE) in T cells of said animal. In the transgenic animal of the present invention, the protein has an inhibitory effect on positive selection of thymocytes in female TCR transgenic mice. Generally, the transgenic mouse has a decreased number of DP and CD8+ thymocytes expressing the $D^b$/HY reactive transgenic TCR and an increased number of CD4 thymocytes expressing an endogenously rearranged TCR The ΔNur77 transgenic mouse of the present invention has various utilities. These mice overexpress the DNA binding domain of Nur77 without the transactivating domain. Therefore, the binding of Nur77 is blocked as is the binding of other members of the Nur77 family. Recently, the Nur77 knockout mouse was shown to have no effect with regard to T cell signaling, proliferation and apoptosis and therefore there is likely to be a family of proteins homologous to Nur77 which use the same DNA binding domain. Blocking of the DNA binding domain, as demonstrated in the ΔNur77 transgenic mouse of the present invention, has a greater inhibitory effect that removal of one member of the Nur77 family.

The ΔNur77 transgenic mouse of the present invention or T cell lines derived from this mouse are useful as a model for defective apoptosis after T cell signaling. High affinity signaling through the T cell receptor is thought to lead to apoptosis but the mechanism is unknown. Thus, the ΔNur77 transgenic mouse of the present invention or cell lines derived therefrom, may be used by a person having ordinary skill in this art to analyze the consequences of defective T cell apoptosis after strong T cell receptor signaling.

Specific diseases are related to apoptosis or defective apoptosis after T cell receptor signaling. Certain autoimmune diseases appear to result from the failure of high affinity T cell receptor interactions to reduce apoptosis. Therefore, one application of cell lines or ΔNur77 transgenic mice of the present invention would be to specifically screen for reagents that induced apoptosis after T cell receptor signaling in the presence of the ΔNur77 protein. Such a drug would skew the immune system toward apoptosis and the removal of autoimmune cells.

A second disease that is triggered after T cell receptor signaling and T cell activation is apoptosis of CD4$^+$ T cells related to AIDS. Thus, the ΔNur77 transgenic mouse of the present invention or cell lines derived therefrom, could be used to study if inhibition of the TCR-Nur77 apoptosis pathway in ΔNur77 transgenic mice reduces apoptosis using the signaling pathway of the AIDS virus. This would be carried out using a mouse model for AIDS and subsequently, a human ΔNur77 construct in human cell lines infected with the AIDS virus and stimulation through TCR/CD3.

The present invention also discloses a novel double transgenic mouse. That is the present invention demonstrates the ΔNur77 transgenic mouse backcrossed with the $D^b$/HY T cell receptor transgenic mouse. These mice produce increased numbers of self-reactive T cells in the thymus. These cells migrate to the lymph node and the spleen, undergo a T cell receptor-mediated proliferation and then subsequently undergo apoptosis. Apoptosis is related to upregulation of Fas and the Fas ligand. Therefore, the ΔNur77 transgenic mouse backcrossed to the $D^b$/HY T cell receptor transgenic mouse provides a novel and highly effective in vivo model for analysis of the events occuring when autoreactive T cells undergo tolerance though the Fas/Gas ligand apoptosis sytem. The T cells can be easily followed using antibodies for Fas and the T cell receptor. This model could therefore be used to screen for compounds that either up or downmodulate the Fas/Fas ligand apoptosis system. This model is especially useful since the in vivo Fas/Fas ligand apoptosis system is involved in its entirety and therefore a compound that affects this system at the level of Fas ligand production, Fas expression or Fas apoptosis signaling can be detected using this model.

The following examples are given for the purpose of illustrating various embodiments of the invention and are not meant to limit the present invention in any fashion.

EXAMPLE 1
Production of Transgenic Mice Expressing the Truncated Nur77 Gene

The mouse Nur77 1200 bp cDNA fragment corresponding to nucleotides (nt) 794–1993 and encoding the truncated mouse Nur77 at residues from 229 for Met to 601 for Phe was amplified by RT-PCR, using normal mouse thymus RNA as a template. The primers used for PCR were 5'-CCACCATGCCAGCAGCTTTC-3' (SEQ ID No. 1) and 5'-GGATCCGTGGGCTATAGGCT-3' (SEQ ID NO:2) (complementary to nt 1977–1993). The italicized nucleotides are not derived from the mouse Nur77 cDNA sequence but added to a constitute eukaryotic translation consensus sequence (underlined) in front of a AUG for Met or is the sequence (underlined) for the BamHI restriction site. The amplified Nur77 cDNA fragment was directly subcloned into PCR TM vector (Invitrogen, San Diego, Calif.). The insert Nur77 cDNA was confirmed by a standard DNA sequencing technique. The truncated Nur77 capable of binding to the homologous Nur77 DNA response element was excised with BamHI and cloned into p913Cβ1E vector (52, 53). The TCR β chain enhancer has been demonstrated to result in T cell-specific expression. The expression constructed was excised and used to produce transgenic mice as previously described (53). TCR αβ TCR transgenic mice reactive with $D^b$/HY antigen (Tg71) were obtained as previously described (54) and backcrossed with the ΔNur77 transgenic mice.

EXAMPLE 2
Southern Blot Analysis of the ΔNur77 Transgene

Tail DNA was prepared and digested with the indicated restriction enzymes. Approximately 10 μg of the digested DNA was separated on a 0.7% agarose gel, blotted to a nylon membrane, and hybridized with a $^{32}$P-labelled full-length Nur77 cDNA probe.

EXAMPLE 3
Nuclear extract preparation

Nuclear extract was prepared from single cell suspensions of thymocytes of ΔNur77 transgenic mice and mice having no transgene, respectively as described (55). Thymocytes were cultured in media or stimulated with 100 ng/ml phorbol myristic acetate (PMA) (Calbiochem, San Diego, Calif.) and 500 μg/ml ionomycin (Calbiochem, San Diego, Calif.) for 6 hours. The protein concentration was determined by BCA protein assay reagent kit (Pierce, Rockford, Ill.), and aliquots were frozen at −80° C. until the electrophoretic mobility shift assay was performed.

EXAMPLE 4
Electrophoretic Mobility Shift Assay

Oligonucleotides containing the NBRE were synthesized at the University of Alabama at Birmingham (Oligonucleotide Core Facility). They are: sense strand 5'-GGAGTTTTAAAAGGTCATGCTCAATTT-3' (SEQ ID NO:3) and antisense strand 5'-GGAAATTGAGCATGACCTTTTAAAACT-3' (SEQ ID NO:4) (44). The sense and antisense strands were mixed in equal molar amounts, annealed by heating to 100° C. for 2 minutes and slowly cooling at 37° C. for 4 hours 20 nanograms of the double stranded oligonucleotides were end-labeled with [α-$^{32}$P]dCTP by the klenow fragment reaction. The unincorporated [α-$^{32}$P]dCTP was removed by passing the reaction through a STE select-D G25 column (5 prime→3 prime, Inc., Boulder, Colo.). A 0.1 ng (approximately 20,000 cpm) radioactive probe was added to 20 μg of extract protein solution, which had been mixed with 2 μg of poly(dI-dC) and reaction buffer (10 mM Tris, pH 7.5, 1 mM DTT, 100 mM KCl, 1 mM EDTA, 0.2 mM PMSF, 1 mg/ml bovine serum albumin, and 5% glycerol) at 25° C. for 10 minutes (56). In the competition assay, a 100-fold excess of cold (unlabeled) probe was added to the radiolabeled probe before they were placed into the reaction mixture. Following incubation at 25° C. for 20 minutes, the samples were fractionated on a nondenaturing polyacrylamide gel in 0.25 TBE, 5% glycerol. After electrophoresis, the gel was dried by vacuum and autoradiography was carried at −70° C. overnight.

EXAMPLE 5
Northern Blot Analysis

Total RNA was isolated from the thymus, transferred onto nylon nitrocellulose membranes, and probed with a 1.2 Kb Nur77 cDNA fragment or β-actin as control.

EXAMPLE 6
Antibodies

Anti-CD3 (clone: 145.2C11), anti-CD4 (clone: GK 1.5), anti-CD8 (clone: 53-47), anti-TCR (clone: H57), and anti-Fas (clone: Jo2) were purchased from PharMingen (San Diego, Calif.). The anti-$D^b$/HY TCR clonotypic mAb M33 was produced as previously described (24).

EXAMPLE 7
Induction of apoptosis in vivo and in vitro

Thymocyte apoptosis was induced in vivo by injection of 50 μg anti-CD3 or anti-TCR antibody i.p. every day for 3 days and analyzed 12 hours after the last dose or by a single injection of 10 μg dexamethasone i.p. and analyzed 12 hours later. For in vitro induction of apoptosis, the thymocytes were incubated for different time periods on 6-well flat bottom plates (Corning Costar, Cambridge, Mass.), that had been coated with either 10 μg/ml of anti-CD3 or cultured in the presence of 10 μM of dexamethasone (Sigma, St. Louis, Mo.).

EXAMPLE 8
Expression of CD3ζ

Single-cell suspensions of thymocytes were cultured in 6-well flat bottom plates with either anti-CD3 or control antibody for 5 minutes followed by protein extract preparation. Cells ($10^6$) were lysed in lysis buffer (20 mM Tris-HCl [pH 7.5], 0.5% Triton X-100, 1 mM PMSF, 1 μg/ml leupeptin, 1 μg/ml aprotinin) and equivalent amounts of total cellular protein lystates (20 μg) were separated on 10% SDS-polyacrylamide gels, blotted to nitrocellulose membranes (Bio-Rad Laboratories, Hercules, Calif.), and incubated with anti-phosphotyrosine antibody. The blots were counterstained with goat anti-mouse IgG conjugated with alkaline phosphatase, and incubated with NBT/BCIP substrate reagents (Sigma, St. Louis, Mo.).

EXAMPLE 9
T Cell-Mediated Cytotoxicity

Peripheral $CD8^+$ T cells were purified from LN cells using a murine CD8 T cell enrichment column (R&D Systems, Inc.). The purified $CD8^+$ T cells were stimulated with irradiated spleen cells obtained from C57BL/6 male mice in the presence of 50 U/ml of IL-2 for 3 days. Viable cells were collected by centrifugation over Ficoll. Con A stimulated spleen cells from C57BL/6 male or female mice were labeled with $^{51}Cr$ and mixed with stimulated $CD8^+$ T cells at the indicated ratio. After incubation for 8 hours, the $^{51}Cr$ released in the supernatants was measured using a γ-counter (Packard Bell, St. Louis, Mo.) and the specific release calculated using the standard method.

EXAMPLE 10
Assay for Fas ligand activity

Unstimulated LN T cells were incubated with $^{51}Cr$ labeled $Fas^+C57BL/6-+/+$ A20 target cells at different effector/target (E/T) ratios in the presence and absence of 10 μg/ml of a Fc-Fas fusion protein (FasFP)(57). Release of $^{51}Cr$ into the supernatant was assessed 8 hours later using a γ-counter. The specific release was calculated using standard methods.

EXAMPLE 11
Proliferative Response of $D^b$/HY Reactive T Cells

Peripheral $CD8^+$ T cells, purified as described above, were cultured in the presence of 50 U/ml of murine IL-2 (Genzyme, Cambridge, Mass.) for the indicated time with irradiated (3300 rad) syngeneic spleen cells obtained from C57BL/6 male or female mice. For measurement of proliferation, 1 μCi of $^3H$-thymidine was added at 16 hours before harvest.

EXAMPLE 12
Flow Cytometry Analysis

Single cell suspensions of thymocytes or lymph node cells were labeled with optimal concentrations of FITC-conjugated anti-CD8, PE-conjugated anti-CD4, or PE-conjugated anti-Fas (PharMingen, San Diego, Calif.) and biotin-conjugated M33 (24) followed by Tandem-Strepavidin. Viable cells (10,000/sample) were analyzed by flow cytometry on a FACS-Scan (Becton Dickinson, Mountain View, Calif.) equipped with logarithmic scales and the data processed in a Hewlett-Packard (Palo Alto, Calif.) computer. The number of cells in each population was determined by quadrant analysis of contour graphs. 10,000 viable cells were analyzed by FACScan.

EXAMPLE 13
Apoptosis Analysis by Terminal Digoxigenin Nucleotide End Labeling Staining The in situ nick translation method of DNA staining was used for in situ determination of apoptotic cells according to Gavrieli, et al. with slight modification (59). Briefly, $1 \times 10^5$ cells were cytospun onto poly-L-lysine pretreated slides, fixed in 10% formalin for over thirty minutes, and the cells subjected to proteinase K digestion (10 μg/ml at RT for 20 minutes). After extensive washing with $ddH_2O$, a reaction mix containing 0.5 μg/ml terminal deoxynucleotide transferase (TdT), 10 μM digitonigen modified-dUTP, and TdT buffer was applied to the slide. The slides were incubated at 37° C. for 1 hour. The poly-dUTP tail which was synthesized at the broken ends of DNA was detected by AP-conjugated anti-digitonigen antibody and NBT/BCIP substrate. At least 200 cells were counted using light microscopy.

EXAMPLE 14
Bromodeoxyuridine Incorporation in vivo and in situ Staining

Bromodeoxyuridine was purchased from Sigma (B5002) and was diluted to 5 mg/ml in PBS. Mice received i.p. injections with 1 mg bromodeoxyuridine/mouse at 6 hours intervals for four doses and sacrificed I hour after the last injection when LN were removed and frozen in OCT. After the sections were frozen, the slides were fixed in ice-cold ethanol (70%) for 20 minutes, and the DNA denatured by incubation at room temperature for 20 minutes in 3 N HCl with 0.5% Tween-20- (Sigma Chemical Co., St. Louis, Mo.). The slides were then incubated for 3 to 5 minutes with 0.5 ml 0.1 M sodium borate buffer, pH 8.5, followed by two further washes in PBS. The slides were then incubated at room temperature for 30 minutes with FITC-conjugated anti-bromodeoxyuridine mAb (Boehringer Mannheim), washed in PBS, and mounted. Slides were examined and photographed using an Argon ion laser scanning confocal microscope (Molecular Dynamics Model 1000).

EXAMPLE 15
Production of ΔNur77 Transgenic Mice

Six lines of mice carrying ΔNur77 transgenic DNA were produced (FIG. 1A). Digestion of tail DNA with BamHI revealed the expected truncated Nur77 fragment of 1.3 kb, which contained the DNA binding domain without the transactivation domain, as well as the genomic Nur77 bands of higher molecular weight. The transgene copy number varied from approximately 3 in the line designated 5-2F to 10 in the transgenic line designated 4- 3M (FIG. 1A). Expression of the truncated ΔNur77 gene in the transgenic mice was analyzed by northern blot analysis (FIG. 1B). Non-transgenic control mice expressed a Nur77 mRNA transcript of approximately 3.7 kb in both lymphoid and non-lymphoid organs. ΔNur 77 transgenic mice expressed an additional transcript of 5.5 kb, corresponding to the truncated Nur77 gene, and a minigene including the CTβ enhancer. The transgene transcript was expressed highly in the thymus, spleen, and lymph node, but was not expressed in the heart or brain. This result indicated that the expression of ΔNur77 controlled by the CTβ enhancer was confined to the lymphoid organs.

To determine the ability of ΔNur77 protein to bind the corresponding DNA binding motif and compete with endogenous Nur77 protein, gel shift assays were performed with a double-strained oligonucleotide containing the Nur77 binding motif, NBRE. Nuclear extracts were prepared from the thymocytes of non-transgenic and ΔNur77 transgenic mice with and without stimulation with PMA+ionomycin. In the unstimulated thymocytes from non-transgenic mice, there was only minimal expression of the endogenous Nur77 DNA-binding protein indicated by a single high molecular weight gel-shift band (FIG. 1C). The expression of endogenous Nur77 protein was greatly increased at 6 hours after stimulation. In unstimulated thymocytes of ΔNur77 transgenic mice, there was high expression of the ΔNur77 protein as demonstrated by a lower molecular weight gel-shift band.

After PMA+ionomycin, stimulation there was increased expression of both the endogenous Nur77 gel-shift band (band A) and the ΔNur77 gel ghift band (band B). Both of these gel-shift bands were the result of specific interaction with the nerve growth factor I-B response element (NBRE) because the binding could be competitively inhibited by addition of increasing concentrations of unlabeled DNA containing the NBRE but not by an irrelevant DNA oligonucleotide (data not shown). These results indicate that RNA encoding the truncated ΔNur77 binding protein is specifically expressed in the T cells of the transgenic mice, and that the truncated ΔNur77 protein produced in ΔNur77 transgenic mice competitively inhibits the binding of endogenous Nur77 to the NBRE.

Figures 1, 5:
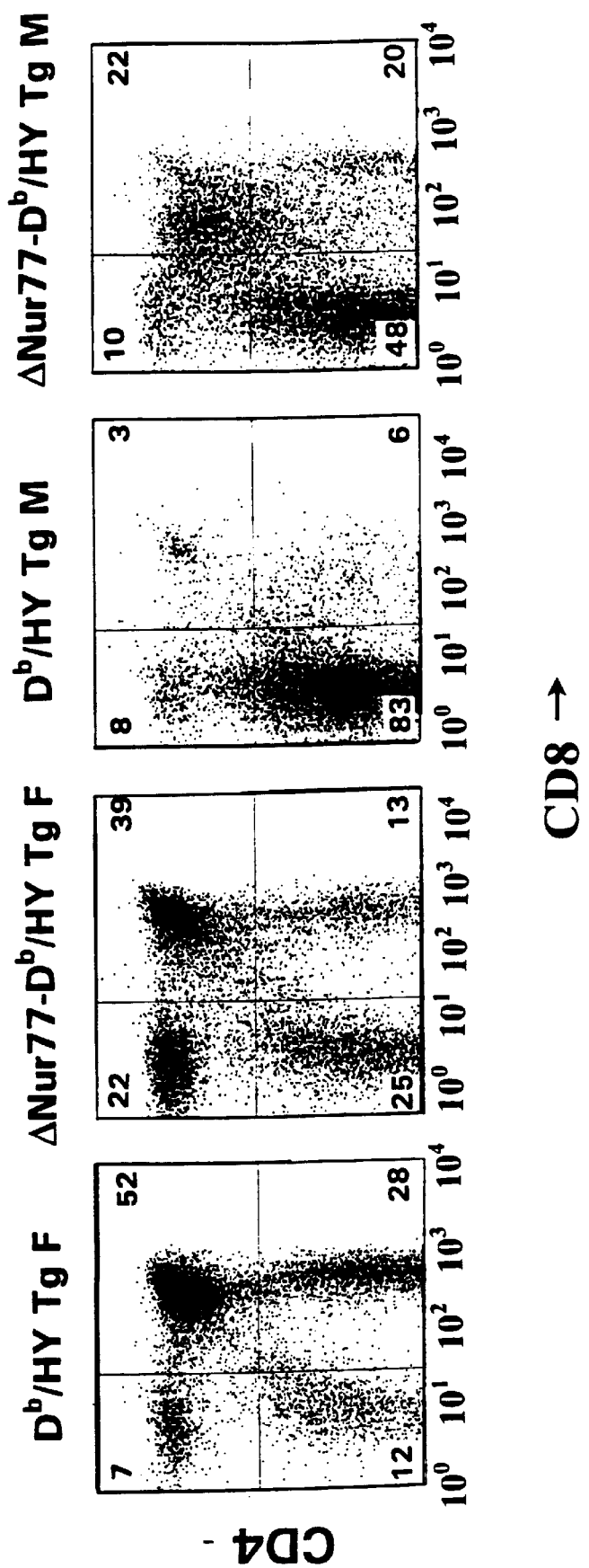
FIG. 5 shows the decreased deletion of $M33^+CD4^+CD8^+$ thymocytes in ΔNur77-$D^b$/HY TCR double Tg male mice. $D^b$/HY TCR single transgenic female or male mice or ΔNur77-$D^b$/HY double transgenic female or male mice were analyzed for expression of CD4, CD8, and the anti-TCR transgene monoclonal Ab M33. The percent of thymocytes expressing high levels of M33 is shown by the cursor and percentage as indicated on the graph. These are representative of typical results for at least three mice analyzed individually.
Figures 2, 5:
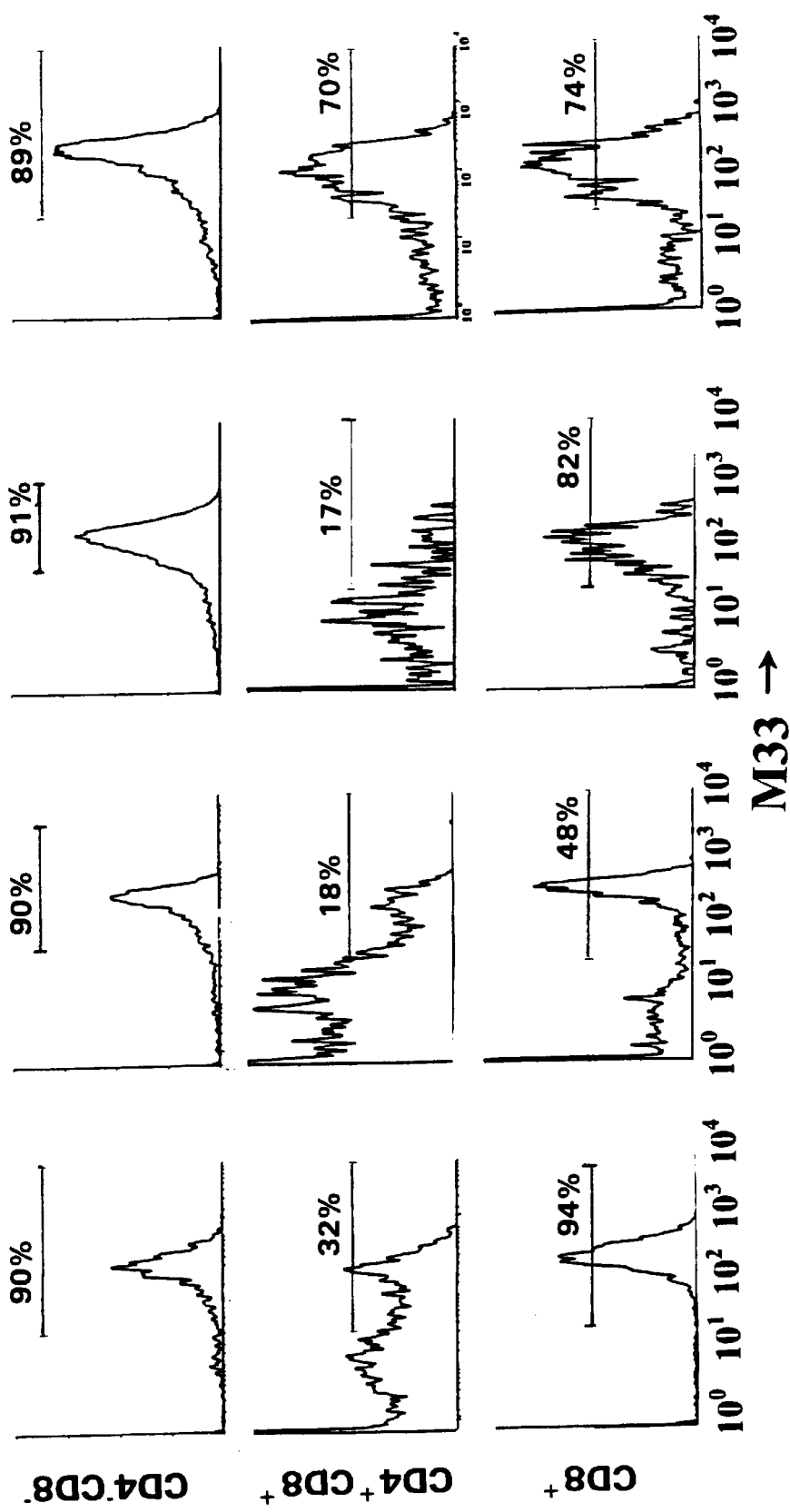
FIG. 2 shows the decreased deletion of $CD4^+8^+$ thymocytes after anti-CD3 or anti-TCR treatment in ΔNur77 transgenic mice. Non-transgenic or ΔNur77 transgenic mice were injected i.p. with 50 mg of either control or anti-CD3 or anti-TCR antibody daily for 3 days and analyzed on day 4. Non-transgenic or ΔNur77 transgenic mice were injected i.p. with dexamethasone (10 µM) and analyzed 12 hours later.

EXAMPLE 16
Inhibition of Anti-TCR/CD3 Mediated Thymocyte Apoptosis in ΔNur77 Transgenic Mice There was no significant abnormality in the development of thymocytes in ΔNur77 transgenic mice (FIG. 2A, Table 1). To characterize the function of the ΔNur77 transgene, it was examined whether apoptosis induced by CD3/TCR signalling was impaired in thymocytes of ΔNur77 transgenic mice. Non-transgenic and ΔNur77 transgenic mice were treated in vivo with control, anti-CD3, or anti-TCR antibodies. Anti-CD3 antibody treatment led to depletion of 86% of the total and 99% of the double positive (DP) thymocytes in non-transgenic mice (Table 1) and reduced the percentage of DP thymocytes to 4% (FIG. 2A). In contrast, anti-CD3-induced deletion of thymocytes was less efficient in ΔNur77 Tg mice, with depletion of 50% of total and 63% of DP thymocytes (Table 1) and reduced the percentage of DP thymocytes to 31% (FIG. 2A). Depletion of $CD4^+$ and $CD8^+$ thymocytes was also inhibited after CD3 antibody treatment of ΔNur77 transgenic whereas deletion of double negative (DN) thymocytes was equivalent in both non-transgenic and ΔNur77-transgenic mice (Table 1).

Although anti-CD3 induced apoptosis was inhibited in ΔNur77-Tg mice, not all pathways of thymocyte apoptosis were inhibited since there was no significant difference in dexamethasone-induced thymocyte deletion comparing non-Tg and ΔNur77-Tg mice (FIG. 2A). Cell sorting and Terminal digoxigenin nucleotide end labeling staining verified that anti-CD3 treatment in vivo resulted in extensive apoptosis of thymocytes (FIG. 2B). To demonstrate that the ΔNur77 transgene did not interfer with early signaling events after CD3/TCR stimulation, tyrosine-phosphorylation of the CD3ζ chain was examined in the peripheral T cells after anti-CD3 crosslinking. There was no significant difference between the extent of tyrosine-phosphorylation of the CD3ζ chain in the T cells of both non-Tg and ΔNur77-Tg mice (FIG. 2C).

To determine if the inhibition of anti-CD3-induced depletion of thymocytes by the ΔNur77 transgene was specific for CD3/TCR signalling, or is a non-specific effect related to an in vivo stress response induced by anti-CD3 treatment, thymocytes obtained from non-transgenic and ΔNur77-transgenic mice were cultured in vitro for different lengths of time with either anti-CD3 or dexamethasone (FIG. 3). There was no difference in the numbers of thymocytes undergoing dexamethasone-induced apoptosis, whereas the thymocytes from ΔNur77-Tg mice exhibited decreased apoptosis when cultured with anti-CD3 (FIG. 3). This result supports the in vivo data indicating that the inhibition of apoptosis of $CD4^+CD8^+0$ thymocytes in ΔNur77 transgenic mice was specific for apoptosis induced by CD3/TCR signalling.

Figure 4A:
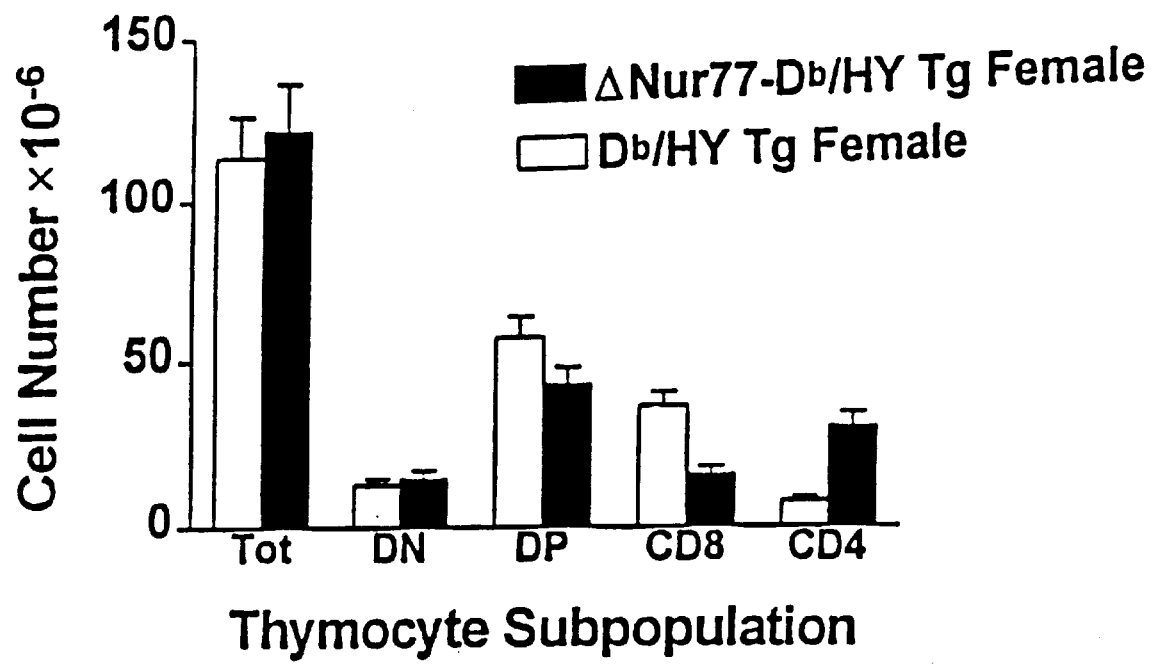
FIG. 4A–B shows the effect of ΔNur77 transgene on thymocyte subpopulations. $D^b$/HY TCR single transgenic female (4A) and male mice (4B) or ΔNur77-$D^b$/HY double transgenic female (4A) and male mice (4B) were analyzed for expression of CD4 and CD8. The numbers of thymocytes in each subpopulation were derived by multiplying the % of thymocytes in each subpopulation by the total number of thymocytes. These are representative of typical results for at least three mice analyzed individually.

EXAMPLE 17
Decreased Deletion of $CD4^+8^+$ Thymocytes in ΔNur77-$D^b$/HY TCR Double Transgenic Male Mice The $D^b$/HY TCR transgenic male mouse has been extensively analyzed as a model for analysis of positive and negative selection. The $D^b$/HY reactive thymocytes exhibit extensive positive selection in $D^b$/HY TCR transgenic female mice and are extensively deleted at the DP stage of thymocyte development in $D^b$/HY TCR transgenic male mice (60–63). To demonstrate that interruption of Nur77/Nurr1 function in ΔNur77 transgenic mice leads to defective positive and negative selection of thymocytes, H-$2^b$ ΔNur77 transgenic mice were backcrossed to $D^b$/HY TCR transgenic C57BL/6 mice. In ΔNur77-$D^b$/HY TCR double transgenic female mice, there were equal numbers of total and DN thymocytes compared to $D^b$/HY TCR transgenic female mice. The ΔNur77 transgene resulted in a significant decrease in the number of DP and $CD8^+$ thymocytes expressing the $D^b$/HY reactive transgenic TCR (detected by the Mab M33) and a significant increase in the number of CD4 thymocytes expressing an endogenously rearranged TCR (FIG. 4A, FIG. 5). Flow cytometric analysis indicated that in ΔNur77-$D^b$/HY TCR double transgenic female mice, only 18% of DP and 48% of CD8 thymocytes expressed the transgenic TCR compared to 32% and 94% in $D^b$/HY TCR transgenic female mice in the absence of the ΔNur77 transgene (FIG. 5). This result suggested that the ΔNur77 transgene may have an inhibitory effect on positive selection of thymocytes in female TCR transgenic mice.

$D^b$/HY TCR transgenic male mice exhibited a 10-fold decrease in total thymocyte number and nearly complete deletion of DP and $CD8^{bright}$ thymocytes due to negative selection of thymocytes bearing the transgenic TCR. Several changes were observed in the thymus of the C57BL/6 ΔNur77-$D^b$/HY TCR double transgenic male mice compared to that of $D^b$/HY TCR transgenic male mice. First,

TABLE 1

Comparison of Thymocyte Deletion after Anti-CD3 Treatment in ΔNur77-Tg and non-Tg control mice.

Figure 4B:
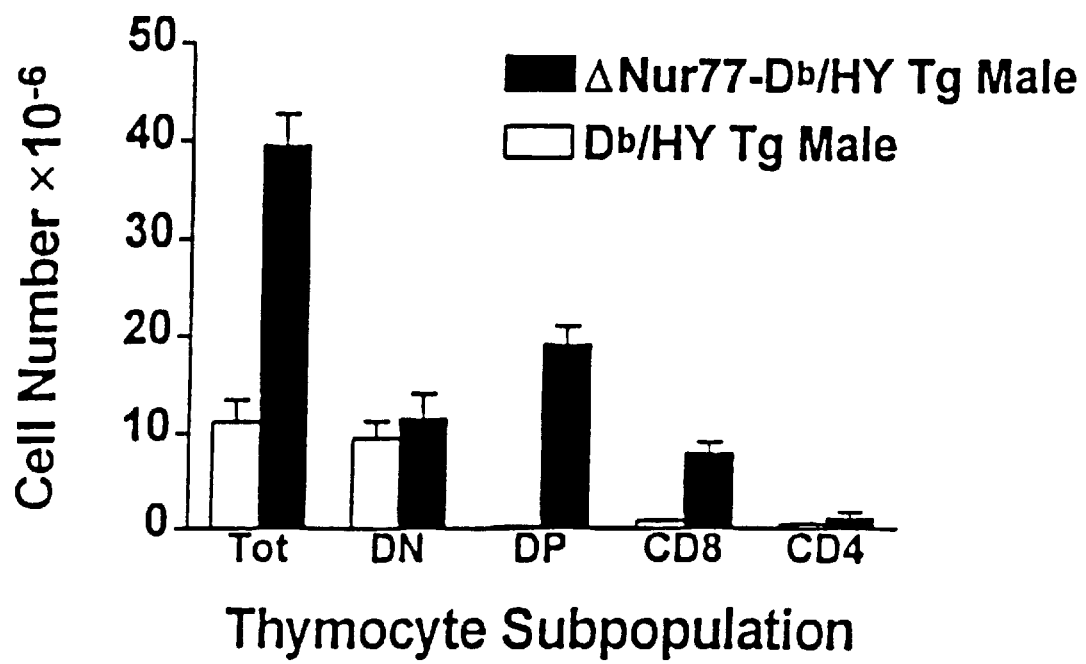

| | Non-Tg | | | | | ΔNur77-Tg | | | | |
|---|---|---|---|---|---|---|---|---|---|---|
| Treatment | Total | DN | DP | $CD4^+$ | $CD8^+$ | Total | DN | DP | $CD4^+$ | $CD8^+$ |
| Control Ab | 114 ± 10 | 5.2 ± 2.2 | 84 ± 12 | 12 ± 2.3 | 8.4 ± 1.5 | 128 ± 12 | 13 ± 2.4 | 82 ± 14 | 21 ± 4 | 14 ± 3 |
| Anti-CD3 | 16 ± 2.8 | 3.5 ± 1.5 | 0.8 ± 0.3 | 8.0 ± 1.5 | 4.8 ± 2.1 | 68 ± 8 | 8.1 ± 1.5 | 30 ± 5 | 19 ± 6 | 11 ± 2.5 |
| % of deletion | 86 | 33 | 99 | 33 | 43 | 50 | 38 | 63 | 10 | 24 | there was a 4-fold increase in total thymocytes that comprised a 20-fold increase in $CD4^{low}CD8^{low}$ DP thymocytes and a 5-fold increase in CD8 thymocytes (FIG. 4B). Second, increased numbers of DP and CD8 thymocytes in $\Delta$Nur77-$D^b$/HY TCR transgenic male mice expressed the transgenic TCR. 70% of $CD4^+CD8^+$ thymocytes were also M33 positive in the $\Delta$Nur77-Tg71 double transgenic male compared to 17% in $D^b$/HY TCR Tg male mice (FIG. 5). Third, in $\Delta$Nur77-$D^b$/HY TCR transgenic male mice, there was the appearance of a substantial number of CD8 thymocytes that exhibited high levels of expression of CD8; 70–80% of these thymocytes expressed the transgenic TCR (FIG. 5). This population was absent in the $D^b$/HY male mice. Taken together, these results indicate that negative selection of the autospecific $D^b$/HY reactive thymocytes was inhibited in $\Delta$Nur77-$D^b$/HY TCR transgenic male mice compared to $D^b$/HY TCR transgenic male mice.

Figure 6:
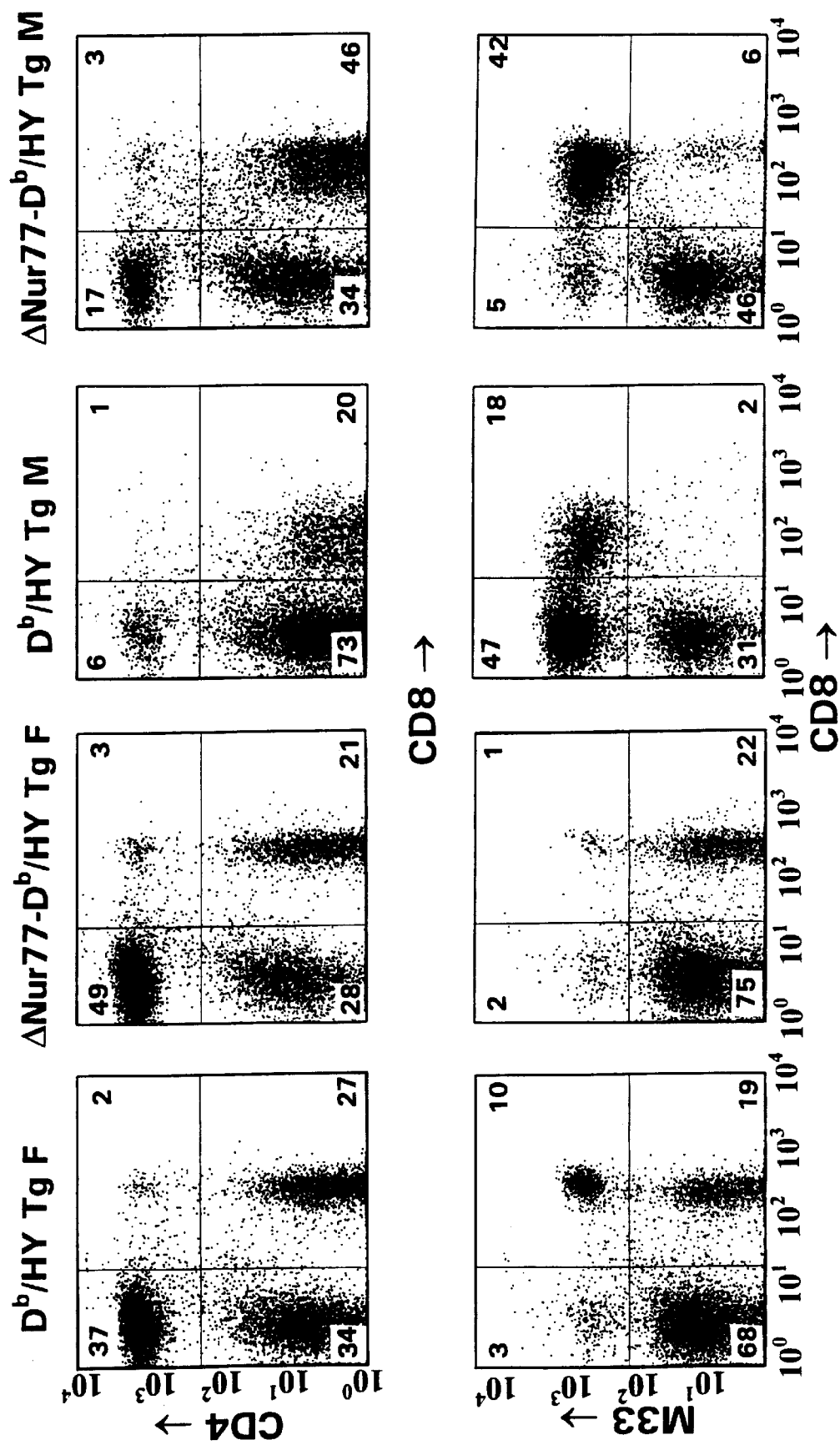
FIG. 6 shows the increased $M33^+CD8^+$ lymph node T cells in the ΔNur77-$D^b$/HY TCR double transgenic male mice. Single cell suspensions from lymph node (LN) was prepared from $D^b$/HY TCR single transgenic female and male mice or ΔNur77-$D^b$/HY TCR double transgenic male mice. Cells were labeled with anti-CD4, anti-CD8 and the anti-clonotypic antibody (M33) recognizing the $D^b$/HY transgenic TCR. Flow cytometry analysis was carried out on 10,000 viable cells. The percentage of cells in each subpopulation marked by the gated cursors is indicated on the graph. These results are representative of three mice analyzed individually.

EXAMPLE 18
Increased $M33^\pm CD8^\pm$ Lymph Node T Cells in the $\Delta$Nur77-$D^b$/HY TCR Double Transgenic Male Mice To determine whether defective thymic clonal deletion leads to the escape of autospecific T cells to the periphery, the phenotype of LN T cells was analyzed. In $D^b$/HY female mice, most of the $CD4^+$ lymph node T cells in the $D^b$/HY TCR transgenic female mice were $M33^-$ indicating expression of endogenously rearranged TCR genes (FIG. 6). Approximately 10% of lymph node cells were $M33^+$ and $CD8^+$. This phenotype was greatly reduced in $\Delta$Nur77-$D^b$/HY TCR Tg female mice in which only 1% of lymph node cells were $CD8^+$ and $M33^+$, whereas most $CD8^+$ T cells expressed an endogenously rearranged TCR transgene (FIG. 6). In the $D^b$/HY male mice, 47% of lymph node cells were $CD4^-CD8^-$ but expressed equivalent levels of the M33 TCR transgene as observed in female mice. In these mice, peripheral lymph node cells expressed down modulated levels of CD8 and also expressed the $D^b$/HY TCR transgene (FIG. 6). In the $\Delta$Nur77 $D^b$/HY TCR double transgenic male mice, there was a significant increase in the total number of cells, and $M33^+CD8^+$ lymph node T cells, but a decreased number of $M33^{+CD}4^-CD8^-$ T cells (TABLE 2). Compared to $D^b$/HY transgenic male mice, most $M33^+$ T cells expressed intermediate to high levels of CD8 (FIG. 6).

TABLE 2

Phenotype of LN T cell in $\Delta$Nur77-Tg71 Tg mice

| Mouse | Sex | n | Total§ | $M33^+CD8^{+\dagger}$ | $M33^+CD8^{-\dagger}$ |
|---|---|---|---|---|---|
| Non-Tg | M | 5 | 1.9 ± 0.5 | — | — |
| $\Delta$Nur77 Tg | M | 5 | 2.0 ± 0.4 | — | — |
| Tg71 | M | 5 | 0.5 ± 0.1 | 0.09 ± 0.01 | 0.25 ± 0.03 |
| $\Delta$Nur77-Tg71 | M | 5 | 1.4 ± 0.3 | 0.68 ± 0.07 | 0.06 ± 0.01 |
| Non-Tg | F | 5 | 1.8 ± 0.5 | — | — |
| $\Delta$Nur77 Tg | F | 5 | 1.9 ± 0.6 | — | — |
| Tg71 | F | 5 | 1.5 ± 0.3 | 0.2 ± 0.05 | 0.08 ± 0.02 |
| $\Delta$Nur77-Tg71 | F | 5 | 1.7 ± 0.4 | 0.08 ± 0.02 | 0.06 ± 0.01 |

§ Total of 2 axillary and 2 inguinal lymph node per mouse. All mice were 8–10 weeks of age. Total represents the mean±SEM of 5 mice per group assayed separately. †Number of LN T cells expressing either the $D^b$/HY TCR$\alpha\beta$ recognized by the anti-clonotypic mAb, M33 or CD8. The number was derived by multiplying the percent of gated cells after flow cytometry by the total number of LN cells. The number represents the mean±SEM of T cells with the indicated surface marker of 5 mice per group assayed separately.

Figure 7A:
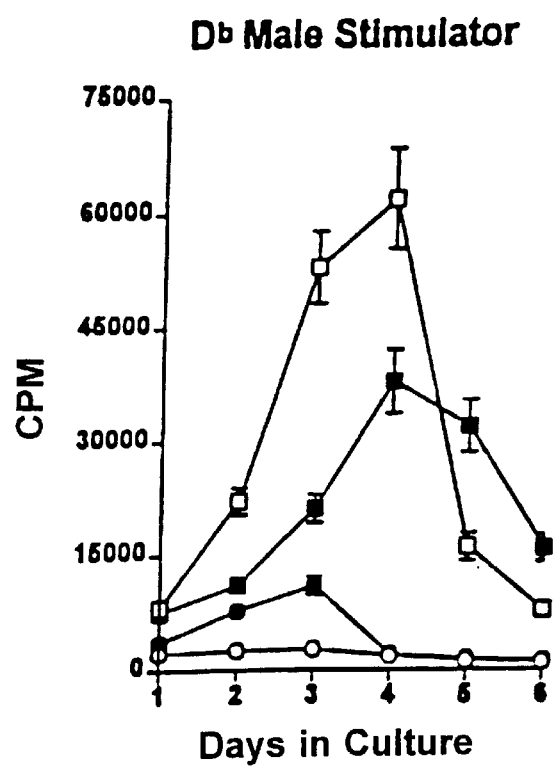
FIG. 7A–D shows the proliferation and cytotoxicity of lymph node T cells. Lymph node (LN) T cells from the indicated single or double Tg mice were purified by negative selection after passing over a T cell column. Proliferation was assayed after culture of purified LN T cells with irradiated $D^b$ male (A) or $D^b$ female (C) stimulator cells for the indicated time. Equal numbers of T cells were used at different effector/target (E/T) ratios to lyse $^{57}$Cr-labeled $D^b$ male (B) or $D^b$ female (D) target cells. The percent of specific lysis or proliferation is indicated as the mean±SEM for at least three individual mice analyzed in triplicate.
Figure 7B:
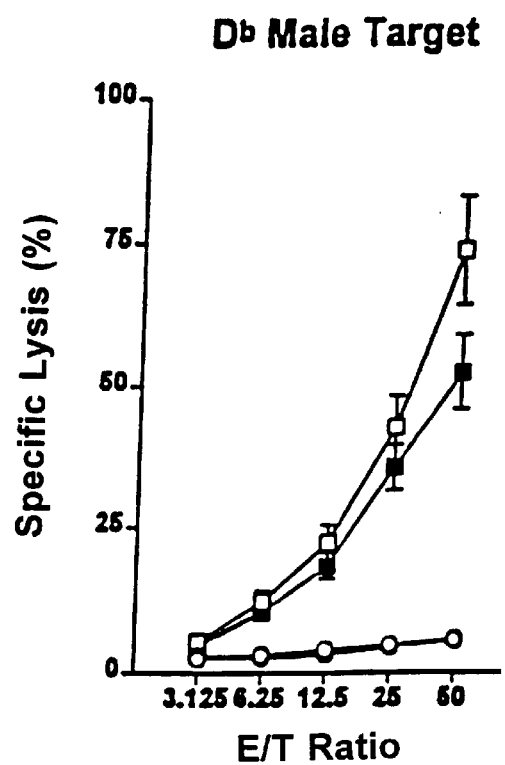
Figures 7C, 7D:
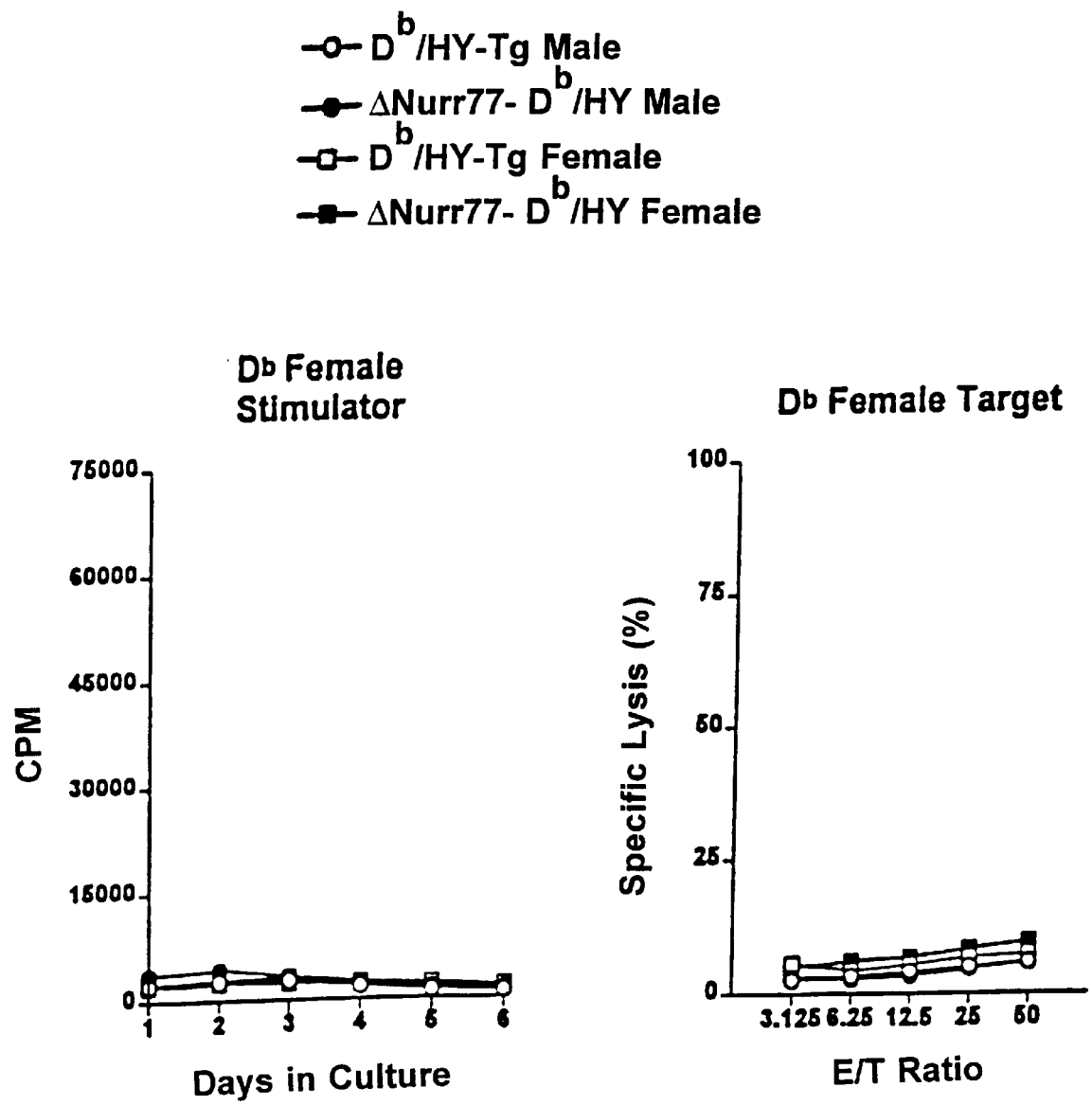

EXAMPLE 19
Tolerance of Lymph Node T Cells in $\Delta$Nur77-$D^b$/HY TCR Tg Male Mice To determine if the increased numbers of $CD8^+$ $M33^+$ lymph node T cells in the double transgenic male mice exhibited loss of tolerance, proliferation was analyzed using irradiated $D^b$ male stimulator cells (FIG. 7A). The proliferative response was greatly reduced in both $D^b$/HY and $\Delta$Nur77-$D^b$/HY male Tg mice compared to female Tg mice (FIG. 7). Specific lysis was assayed using chromium-labeled $D^b$ male target cells (FIG. 7B). There was low specific lysis of target cells by lymph node T cells from both $D^b$/HY and $\Delta$Nur77-$D^b$/HY TCR male transgenic mice compared to female Tg mice (FIG. 7B). The proliferative and cytotoxic response was specific to $D^b$/HY antigen as there was no increased specific proliferation or lysis when $D^b$ female cells were used as stimulators or targets (FIG. 7C and D).

EXAMPLE 20
Increased in vivo Activation and Apoptosis in the LN of $\Delta$Nur77-$D^b$/HY Mice In spite of inefficient thymic clonal deletion in $\Delta$Nur77-$D^b$/HY Tg male mice, peripheral T cell tolerance is maintained, suggesting there are alternative mechanisms to maintain T cell tolerance. Fas and Fas ligand mediated apoptosis has been shown to play a critical role in activation-induced apoptosis of peripheral T cells (64–67). To determine whether activation-induced apoptosis in the periphery compensated for defective thymic clonal deletion, in vivo activation and apoptosis were examined in the LN by bromodeoxyuridine labeling of cycling cells and Terminal digoxigenin nucleotide end labeling staining respectively (FIG. 8A). There was increased uptake of bromodeoxyuridine by LN T cells in the $\Delta$Nur77-$D^b$/HY TCR transgenic male mice compared to the $D^b$/HY TCR transgenic male mice and $D^b$/HY TCR transgenic female mice with or without the $\Delta$Nur77 transgene (FIG. 8A). This increased activation was specific for the $D^b$/HY antigen as no increased bromodeoxyuridine uptake was observed in $\Delta$Nur77-$D^b$/HY TCR double-transgenic female mice.

In vivo apoptosis was also analyzed by in situ Terminal digoxigenin nucleotide end labeling staining of LN. There was significantly increased apoptosis in the LN of $\Delta$Nur77-$D^b$/HY TCR male mice compared to $D^b$/HY TCR single transgenic male mice and $\Delta$Nur77-$D^b$/HY TCR double-transgenic female mice (FIG. 8A). These results indicate that there was increased in vivo activation and apoptosis in the LN of $\Delta$Nur77-$D^b$/HY TCR transgenic male mice and suggest that tolerance might be maintained by increased activation-induced apoptosis in the periphery of $\Delta$Nur77-$D^b$/HY TCR double transgenic male mice.

Figure 8B:
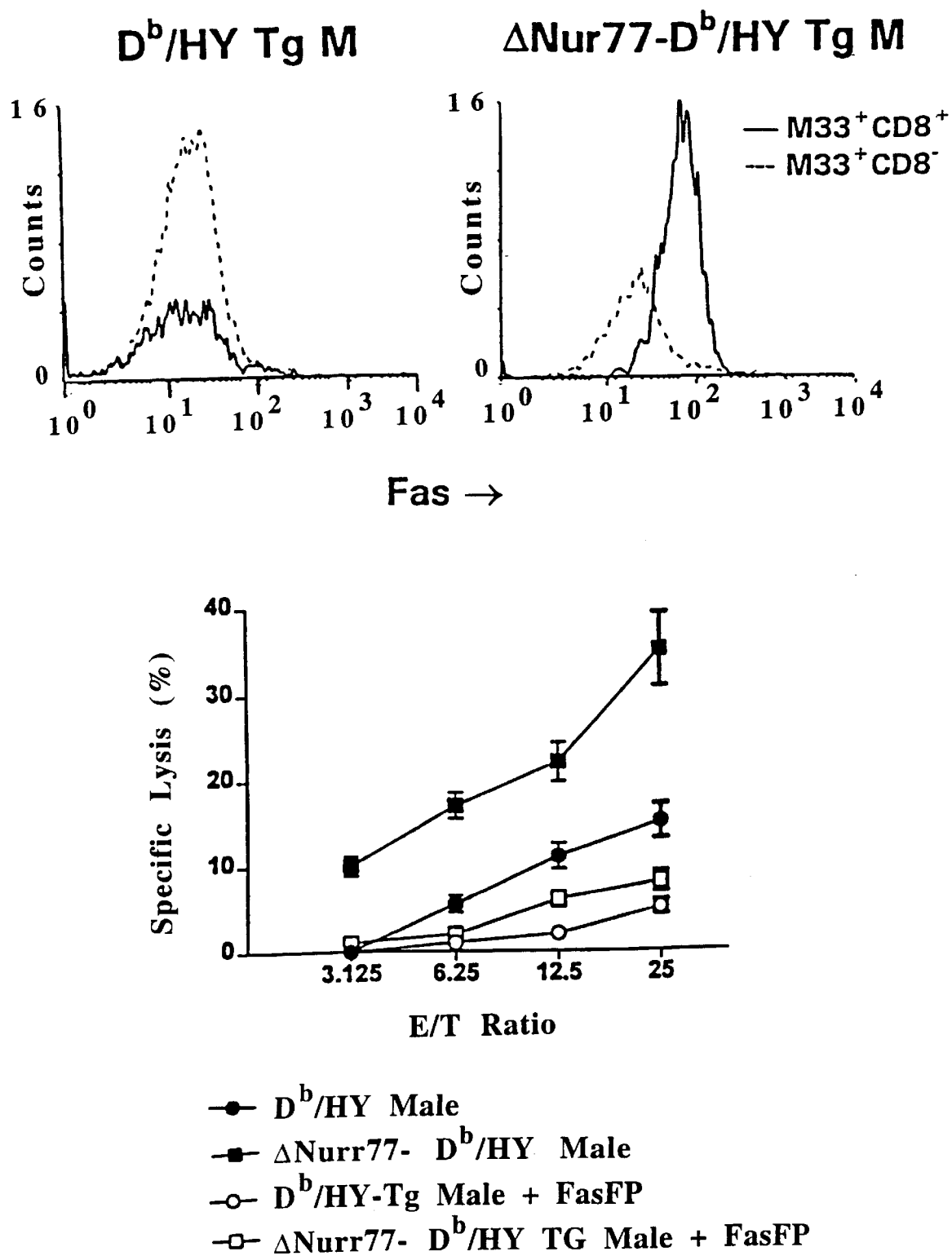

Fas and FasL expression by LN T cells from $D^b$/HY TCR single and $\Delta$Nur77-$D^b$/HY TCR double transgenic male mice was determined (FIG. 8B). Previous studies have shown that two major T cell populations express the transgenic $D^b$/HY TCR in $D^b$ male mice, one is $CD4^-CD8^-$ and the other is $CD8^{dull}$. Both T cell populations are functionally anergic. Fas was expressed at a low level in both T cell populations of $D^b$/HY male mice. In contrast, Fas expression was increased on the self-reactive $M33^+CD8^+$ T cells but not on the $M33^+CD8^-$ T cells of $\Delta$Nur77-$D^b$/HY TCR double transgenic male mice. Fas ligand expression was determined by culture of different effector/target (E/T) ratio of T cells from the LN of different mice with a $^{57}Cr$ labeled Fas sensitive cell line (FIG. 8B). There was increased FasL production by T cells from the $\Delta$Nur77-$D^b$/HY TCR double transgenic male mice compared with the $D^b$/HY TCR transgenic male mice which could be inhibited by a soluble Fas fusion protein (FasFP). These results indicate that in ΔNur77-D$^b$/HY TCR Tg male mice, peripheral tolerance was likely maintained by a Fas mediated AICD mechanism.

Nur77 mutant mice were recently found to not exhibit defective apoptosis after anti-CD3 induced death and did not exhibit defective thymocyte development or apoptosis after crossing with the D$^b$/HY TCR transgenic mice (51). Results of previous investigators and the present results indicate that inhibition of the DNA binding by over-expression of the NBRE-binding portion of Nur77 results in defective apoptosis (48, 49). Nuclear factors capable of binding to the NBRE consist of several members of a superfamily sharing homology of the DNA binding domain. The NBRE response element consensus sequence is AAAGGTCA and is composed of two 5' adenine nucleotides and the half-site of the estrogen response element (41–47). The second member of this family has been recently isolated from a human lymphoid cell line PEER after induction of apoptosis and is refereed to as TINUR (transcriptionally inducible nuclear receptor) in human and Nurr1 in mouse (50). Transcriptionally inducible nuclear receptor has a highly homologous DNA binding domain to Nur77 as do other members of this family described in other species, but there was little homology in the N-terminal effector function region. TCR mediated signaling results in early induction of Nur77 which peeks after 1 hour, and later induction of transcriptionally inducible nuclear receptor which peeked at 24 hrs in PEER cells (50). Expression of transcriptionally inducible nuclear receptor also correlated with apoptosis which was also maximal 24 hours after anti-TCR signaling. The difference in the kinetics of peak expression of Nur77 and transcriptionally inducible nuclear receptor expression lead to the conclusion that different genes may play complementary roles in T cell activation or apoptosis. The preferential inhibition of apoptosis of CD4$^+$8$^+$ thymocyte by blocking the NBRE, combined with previous results that Nur77 knockout does not inhibit apoptosis of CD4$^+$8$^+$ thymocytes support the conclusion that other factors that interact with the NBRE such as Nurr1/TINUR plays a role in apoptosis of thymocytes.

Although Nurr1 and Nur77 has been shown to be important in TCR-mediated apoptosis in T cell hybridomas in vitro, the importance of Nur77 and Nurr1 in negative selection and clonal deletion in the thymus has not been established. The present invention demonstrates that apoptosis of CD4$^+$CD8$^+$ (DP) thymocytes after TCR/CD3 signaling is inhibited in the ΔNur77 transgenic mice and suggest that this event is dependent on DNA-binding factors including Nurr1 and Nur77. Apoptosis after anti-TCR or anti-CD3 is highly dependent on a functional NGFI-B/Nur77 pathway (48, 49). Negative selection was also analyzed in the D$^b$/HY TCR transgenic male mice. The presence of the ΔNur77 transgene resulted in increased numbers of CD4$^+$CD8$^+$ thymocytes and the appearance of more mature CD8$^+$ thymocytes both expressing the autospecific D$^b$/HY transgenic TCR. The increase in the production of CD4$^+$8$^+$ (double positive) thymocytes in D$^b$/HY male mice was not due to increased positive selection for these cells. This is supported by a decrease in CD4$^+$8$^+$ thymocytes in the ΔNur77-D$^b$/HY TCR transgenic female mice. The appearance of mature CD8 single positive autospecific thymocytes suggests a deletion defect at a mature stage of thymocyte development. Together, these data strongly suggest that the family of DNA binding proteins including Nurr1 and Nur77 are directly involved in signaling of positive and negative selection during T cell development in the thymus.

After anti-TCR or anti-CD3 crosslinking in vivo, apoptosis of CD4$^+$8$^+$ thymocytes was inhibited in the ΔNur77 transgenic mice. The failure to completely block apoptosis in these mice could be due to the presence of other apoptosis pathways which do not involve the NBRE or due to a "leaky" blockade of the NBRE because of a lack of complete competition of DNA binding sites by the truncated, inactive ΔNur77 protein. The first possibility was favored because in vitro, anti-CD3 apoptosis was not significantly greater than control antibody-induced apoptosis (FIG. 3) providing evidence that in ΔNur77 transgenic mice, anti-CD3 induced apoptosis via the NBRE is functionally inactivated. Other apoptosis pathways exist in the thymus in vivo and these pathways may operate at different developmental stages of thymocytes or in association with different signaling events in addition to anti-CD3. Increased T cell survival during negative selection has been observed in bcl-2/D$^b$/HY TCRαβ double transgenic mice (34–36). Increased survival of unselected thymocytes and inhibition of negative selection of thymocytes was observed in bcl-2/D$^b$/HY TCR female and male mice (34). Another possibility is that the NBRE might be one factor leading to regulation of apoptosis-related genes and also induction of genes such as Bcl-Xs and Bax that down-regulate genes such as bcl-2 that inhibit apoptosis (68–71).

Another important pathway of apoptosis for thymocytes is dexamethasone-induced apoptosis (72, 73). The lack of inhibition of dexamethasone-induced apoptosis in the ΔNur77 transgenic mice is significant since this indicates that there is no competitive inhibition between the Nur77/Nurr1 orphan steroid receptors either at the level of cytoplasmic steroid binding or at the receptor-DNA binding site with glucocorticoids. This lack of inhibition between dexamethasone apoptosis and Nur77/Nurr1 apoptosis indicates apoptosis is mediated by separate independent pathways. Taken together, there are multiple independent pathways of thymocyte apoptosis related to TCR/CD3 signaling that may be affected by inhibition of Nurr1/Nur77 interaction with NBRE.

Functional blockade of the NBRE did not greatly inhibit the T cell activation signal after TCR/CD3 crosslinking. There was normal phosphorylation of the CD3ζ chain in ΔNur77 Tg mice. Also, proliferation after TCR/CD3 mediated activation of LN T cells was increased in the ΔNur77 D$^b$/HY TCR transgenic male mice and was only slightly decreased in T cells from ΔNur77 D$^b$/HY TCR Tg female mice compared to D$^b$/HY single TCR Tg male and female mice, after culture with D$^b$ male stimulator cells (FIG. 7). Proliferation after stimulation was very low in the D$^b$/HY male mice, and this was increased approximately 10-fold in the ΔNur77 D$^b$/HY double transgenic male mice. Increased proliferation could not be accounted for by an increase in the number of M33$^{+CD}$8$^+$ T cells, which were increased only 2-fold. These results suggest that alternative pathways to signal proliferation after stimulation through the TCR/CD3 molecules are present in addition to the ΔNur77 pathway, and these result in nearly normal proliferation after TCR/CD8 signaling in the ΔNur77 transgenic mice.

In ΔNur77 transgenic male mice there was an increase in M33$^{+CD}$8$^+$ T cells in the lymph node which results from inefficient thymic clonal deletion and compensatory increase in LN peripheral expansion followed by clonal deletion. Activation induced apoptosis of non-tolerant T cells is supported by the observation of a specific increase in bromodeoxyuridine incorporation in vivo in Nur77-D$^b$/HY TCR Tg male mice but not in ΔNur77-D$^b$/HY TCR Tg female mice lacking the HY antigen. Also, increased T cell activation was associated with increased apoptosis in ΔNur77-D$^b$/HY TCR Tg male but not ΔNur77-D$^b$/HY TCR Tg female mice. Fas and Fas ligand interaction has been shown to be an important mechanism for activation-induced apoptosis (64–67, 74, 75). Several lines of evidence indicate that this AICD in ΔNur77-$D^b$/HY TCR Tg male mice was due to Fas/Fas ligand interaction. First, apoptosis in vitro could be blocked by the FasFP. Second, Fas expression was increased in the M33$^{+,}$ $^{CD}8^+$ T cells, but not in the M33$^+$, CD8- T cells, of Nur77-$D^b$/HY TCR Tg male mice, consistent with ongoing AICD using a Fas/Fas ligand pathway. Finally, there was increased Fas ligand production by LN T cells from Nur77-$D^b$/HY TCR Tg male but not female mice.

The following references were cited herein:
1. Nossal, G. J. V., *Cell* 76:229–239, (1994).
2. Golstein, P., et al., *Immunol. Rev.* 121:29–65, (1991).
3. Cohen, J. J., et al., *Annu. Rev. Immunol.* 10:267–271, (1992).
4. Lucas, B., et al., *J. Immunol.* 153:53–58, (1994).
5. Punt, J. A., et al., *J. Exp. Med.* 179:709–713, (1994).
6. Page, D. M., , et al.,*J. Immunol.* 151:1868–1880, (1993).
7. Kappler, J. W., et al., *Cell.* 149:273–280, (1987).
8. MacDonald, H. R., et al., *Nature.* 332:40–45, (1988).
9. Berg, L. J., et al., *Nature.* 340:559, (1989).
10. Burkly, L. C., et al., *Science.* 248:1364, (1990).
11. Ferber, I., et al., *Science.* 263:674–676, (1994).
12. Schronrich, G., et al., *J. Immunol.* 151:4098–4105, (1993).
13. Clarke, A. R., et al., *Nature.* 362:849–852, (1993).
14. Lowe, S. W., , et al., *Nature* 362:847–849, (1993).
15. Lee, J. M., et al.,*Proc. Natl. Acad. Sci. USA.* 90:5742–5746, (1993).
16. Nagata, S., et al.,*Science.* 267:1449–1456, (1995).
17. Suda, T., et al.,*Cell.* 75:1169–1178, (1993).
18. Takahashi, T., et al., *Cell.* 76:969–976, (1994).
19. Lynch, D., et al., *Immunity.* 1:131–136, (1994).
20. Watanabe-Fukunaga, R., et al., *Nature.* 356:314–317, (1992).
21. Kotzin, B. L., et al., *J. Exp. Med.* 168:2221–2229, (1988).
22. Singer, P. A., et al.,*J. Exp. Med.* 170:1869–1877, (1989).
23. Mountz, J. D., et al., *J. Immunol.* 144:2159–2166, (1990).
24. Zhou, T., et al., *J. Immunol.* 147:466–474, (1991).
25. Zhou, T., et al.,*J. Exp. Med.* 176:1063–1072, (1992).
26. Bissonnette, R. P., et al., *Nature.* 359:552–554, (1992).
27. Fanidi, A., et al., *Nature.* 359:554–556, (1992).
28. Strasser, A., et al., *Cell.* 67:889–899, (1991).
29. Moore, N.C., et al., *Immunology.* 81:115–119, (1994).
30. Veis, D., et al., *Cell.* 75:229–240, (1993).
31. Katsumata, M., et al., *Proc. Natl. Acad. Sci.* 89:11376–11380, (1992).
32. Siegel, R. M., et al., *Proc. Natl. Acad. Sci.,* 89:7003–7007, (1992).
33. Sentman, C. L., et al., *Cell.* 67:879–888, (1991).
34. Strasser, A., et al., *Proc. Natl. Acad. Sci.* 91:1376–1380, (1994).
35. Lundberg, K., et al., *J. Exp. Med.* 179:1475–1483, (1994).
36. Tao, W., et al., *J. Exp. Med.* 179:145–153, (1994).
37. Milbrandt, J., *Neuron.* 1:183–195, (1988).
38. Hazel, T. G., et al.,*Proc. Natl. Acad. Sci.* 85:8444–8448, (1988).
39. Williams, G. T., et al., *Mol. Cell Biol.* 13:6124–6136, (1993).
40. Abu-Shakra, S. R., et al., *Brain Res. Mol. Brain Res.* 18:216–220, (1993).
41. Law, S. W., et al., *Mol. Endocrinol.* 6:2129–2135, (1992).
42. Davis, I. J., et al., *Mol. Endocrinol.* 7:953–964, (1993).
43. Yoon, J. K., et al., *J. Biol. Chem.* 268:9148–9155, (1993).
44. Wilson, T. E., et al., *Science.* 252:1296–300, (1991).
45. Wilson, T. E., et al., *Science.* 256:107–110, (1992).
46. Wilson, T. E., et al., *Mol. & Cell. Biol.* 13:5794–5804, (1993).
47. Wilson, T. E., et al., *Proc. Natl. Acad. Sci.,* 90:9186–9190, (1993).
48. Liu, Z-G., et al., *Nature.* 367:281–284, (1994).
49. Woronica, J. D., et al., *Nature.* 367:277–280, (1994).
50. Okabe, T., et al., *J. Immunol.* 154:3871–3879, (1995).
51. Lee, S. L., et al., *Science.* 269:532–535, (1995).
52. Kaye, J., et al., *Nature.* 341:746–749, (1989).
53. Kaye, J., et al., *Nature.* 336:580–583, (1988).
54. Mountz, J. D., et al., *J. Exp. Med.* 172:1805–1817, (1990).
55. Deryckere, F., et al., *BioTechniques.* 16:405–409, (1994).
56. Garner, M., et al., *Nucleic Acids Res.* 9:3047–3059, (1982).
57. Cheng, J., et al., *Science.* 263:1759–1762, (1994).
58. Zhou, T., et al., *J. Immunol.* 150:3651–3667, (1993).
59. Gavrieli, Y., et al., *J. Cell Biol.* 119:493–501, (1992).
60. Kisielow, P., et al., *Nature.* 333:742–745, (1988).
61. Kisielow, P., et al., *Nature.* 335:730–734, (1988).
62. von Boehmer, H., *Annu. Rev. Immunol.* 8:531–555, (1990).
63. Teh, H-S., et al., *J. Exp. Med.* 169:795–806, (1989).
64. Ju, S. T., et al., *Nature.* 373:444–448, (1995).
65. Brunner, T., et al., *Nature.* 373:441–444, (1995).
66. Dhein, J., et al., *Nature.* 373:438–441, (1995).
67. Alderson, M. R., et al.,*J. Exp. Med.* 181:71–77, (1995).
68. Kiefer, M. C., et al., *Nature.* 374:736–739, (1995).
69. Yang, E., et al., *Cell.* 80:285–291, (1995).
70. Yin, X. M., et al., *Nature.* 369:321–323, (1994).
71. Oltvai, Z. N., et al., *Cell.* 74:609–619, (1993).
72. Yang, Y., et al., *J. Exp. Med.* 181:1673–1682, (1995).
73. Vacchio, M. S., et al., *J. Exp. Med.* 179:1835–1846, (1994).
74. Kabelitz, D., et al.,*Immunol. Today.* 14:339–340, (1993).
75. Green, D. R., et al., *Curr. Opin. Immunol.* 6:476–487, (1994).

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A transgenic mouse whose genome comprises a transgene, wherein said transgene comprises a truncated Nur77 (ΔNur77) gene operably linked to a TCRβ enhancer, wherein said truncated Nur77 gene encodes a DNA binding protein of Nur77, and wherein said transgene is expressed in the cells of said mouse such that said mouse exhibits defective T cell apoptosis mediated by T cell receptor signaling.

2. The transgenic mouse of claim 1, wherein said TCRβ enhancer results in early expression of the transgene in thymocytes.

3. The transgenic mouse of claim 1, wherein expression of said ΔNur77 transgene produces a DNA binding protein without a transactivation domain, said protein being produced from an about 5.5 kb ΔNur77 transcript.

4. The transgenic mouse of claim 1, wherein said ΔNur77 transgene is expressed in the thymus, spleen, and lymph node but is not expressed in the heart or brain.

5. The transgenic mouse of claim 1, wherein the protein produced from said ΔNur77 transgene competitively inhibits the binding of endogenous Nur77 protein to the nerve growth factor I-B response element (NBRE) in T cells of said mouse.

6. A double transgenic mouse, wherein said double transgenic mouse is made by a process comprising backcrossing the ΔNur77 transgenic mouse of claim 1 with a $D^b$/HY T cell receptor-α/β transgenic mouse, wherein expression of the transgenes from both parental strains in said double transgenic mouse results in one or more of a phenotype selected from the group consisting of:

i) a five-fold increase in the number of thymocytes expressing self-reactive $D^b$/HY TCR-α/β relative to the $D^b$/HY TCR-α/β parental strain, ii) a ten-fold increase in CD4+CD8+ thymocytes expressing the TCR-α/β transgene relative to the $D^b$/HY TCR-α/β parental strain, iii) an eight-fold increase in CD8+, $D^b$/HY TCR-α/β T cells in the lymph nodes relative to male mice of the $D^b$/HY TCR-α/β parental strain, and iv) increased activation and apoptosis of T cells associated with increased expression of Fas and Fas ligand in the lymph nodes relative to the $D^b$/HY TCR-α/β or the ΔNur77 parental strain.

7. The double transgenic mouse of claim 6, wherein said mouse produces higher numbers of self-reactive T cells in the thymus than does a ΔNur77 transgenic male mouse.

8. The double transgenic mouse of claim 6, wherein said mouse exhibits deficient clonal deletion of self-reactive thymocytes as demonstrated by a ten-fold increase in the CD4+CD8+ thymocytes that express the TCR-αβ transgene.

9. The double transgenic mouse of claim 6, wherein said mouse exhibits increased activation and apoptosis of lymph node T cells associated with increased expression of Fas and Fas ligand when compared with activation and apoptosis of lymph node T cells and expression of Fas and Fas ligand in a ΔNur77 transgenic male mouse.

10. A method of using the double transgenic mouse of claim 6, comprising the steps of:

a) detecting autoreactive lymph node T cells using antibodies directed against Fas and the T cell receptor; and b) screening for compounds that either up or down modulate the Fas/Fas ligand apoptosis system using the detection method described in (a), wherein the results of (a) and (b) provide an in vivo model for analysis of autoreactive T cells undergoing tolerance through the Fas/Fas ligand apoptosis system.

11. The double transgenic mouse of claim 6, wherein the protein produced from the ΔNur77 transgene inhibits positive selection of thymocytes relative to a transgenic ΔNur77 female mouse.

12. The double transgenic mouse of claim 11, wherein said mouse produces a decreased number of CD4+CD8+ thymocytes and CD8+ thymocytes expressing the reactive $D^b$/HY TCR-α/β transgene, and an increased number of CD4 thymocytes expressing an endogenously rearranged TCR, relative to a ΔNur77 transgenic female mouse.

* * * * *